United States Patent [19]

Lin

[11] Patent Number: 5,525,599
[45] Date of Patent: Jun. 11, 1996

[54] 7-SUBSTITUTED-AMINO-3-SUBSTITUTED-3-CEPHEM-4-CARBOXYLIC ACIDS

[75] Inventor: Ho-Shen Lin, Indianapolis, Ind.

[73] Assignee: Eli Lilly and Company, Indianapolis, Ind.

[21] Appl. No.: 95,383

[22] Filed: Jul. 21, 1993

[51] Int. Cl.⁶ .................... C07D 498/04; A61K 31/535
[52] U.S. Cl. .............................. 514/210; 540/301
[58] Field of Search .................... 540/205, 301; 514/210

[56] References Cited

U.S. PATENT DOCUMENTS

| | | | |
|---|---|---|---|
| 4,645,769 | 2/1987 | Shibahara et al. | 514/210 |
| 4,661,480 | 4/1987 | Milns | 540/301 |
| 4,950,662 | 8/1990 | Fujii et al. | 540/205 |
| 4,957,912 | 9/1990 | Diartends et al. | 514/210 |
| 5,019,571 | 5/1991 | Cook et al. | 514/210 |
| 5,077,287 | 12/1991 | Ternansky | 514/210 |
| 5,084,447 | 1/1992 | Ternansky | 514/80 |
| 5,128,336 | 7/1992 | Cook et al. | 514/210 |
| 5,158,946 | 10/1992 | Gasson et al. | 540/205 |

FOREIGN PATENT DOCUMENTS

0495584A2  1/1992  European Pat. Off. .

*Primary Examiner*—Nicholas Rizzo
*Attorney, Agent, or Firm*—Janet T. McClain; James J. Sales

[57] ABSTRACT

The invention provides compounds of the formula

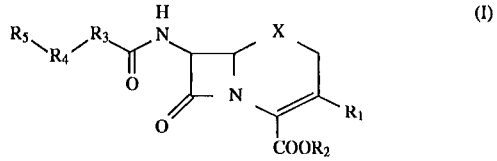

wherein X is $CH_2$, S or O;

$R_1$ is a 3 position substituent such as hydrogen, hydroxy, halo, trifluoromethyl, $C_2F_5$, $C_1$–$C_6$ alkyl, $C_1$–$C_6$ substituted alkyl, $C_1$–$C_6$ alkenyl, $C_1$–$C_6$ alkynyl, $CH_2O(CO)R'$, $CH_2O(CO)NH_2$, $CO_2R'$, thio($C_1$–$C_6$)alkyl, thio($C_1C_6$)alkenyl, oxo($C_1$–$C_6$)alkyl, phosphine oxide, quaternary ammonium group, substituted or unsubstituted thiazolothio, or oxo($C_1$–$C_6$)alkenyl;

wherein R' is hydrogen, $C_1$–$C_6$ alkyl, or $C_1$–$C_6$ alkenyl;

$R_2$ is hydrogen or a carboxy protecting group;

$R_3$ is

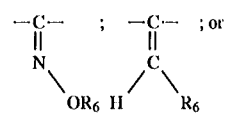

$(CH_2)_n$;

wherein $R_6$ is hydrogen Me, $CH_2F$, $CF_3$, $C_2H_5$, $CH_2CH_2F$, $CH_2CF_3$, $C_2F_5$, $CH_2CO_2R'$, $CH_2CONH_2$, $C(Me)_2CO_2R'$, or $C(Me)_2CONH_2$; and n is 0–5;

$R_4$ is

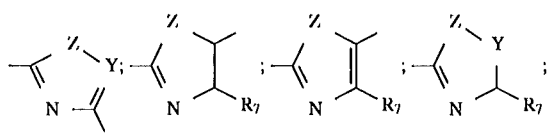

wherein Z is O, S, NH, or $CH_2$; Y is CH or N; and $R_7$ is hydrogen, $C_1$–$C_6$ alkyl, $CONH_2$, or $CO_2R'$; and $R_5$ is

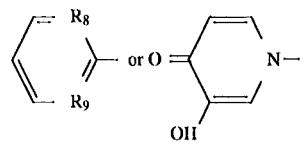

wherein $R_8$ is CH, N, COH, CO($C_1$–$C_6$ alkyl) CSH, or $CNH_2$; and $R_9$ is $R_8$ as defined; said $R_5$ optionally substituted 1–4 times with halo, OH, SH, $NH_2$, $NO_2$, $CH_3$, $C_2H_5$, $CO_2R'$, $CONH_2$, $SO_3H$, or $SO_2NHR'$; and salts thereof. Also, pharmaceutical formulations and methods for treating bacterial infections in man or other animals using the above compounds are disclosed.

3 Claims, No Drawings

7-SUBSTITUTED-AMINO-3-SUBSTITUTED-3-CEPHEM-4-CARBOXYLIC ACIDS

BACKGROUND OF THE INVENTION

This invention relates to 1-carba(1-dethia)cephalosporin, 1-oxa(1-dethia)cephalosporin, and cephalosporin antibiotics, to pharmaceutical formulations comprising the antibiotics, and to a method for the treatment of infectious diseases in man and animals.

Although many safe and potent antibiotics of the β-lactam class are known and used clinically, the research into this class of compounds continues in an effort to find antibiotics with improved efficacy, particularly against microorganisms insensitive or resistant to the known antibiotics, such as methicillin-resistant microorganisms.

SUMMARY OF THE INVENTION

The compound of the formula

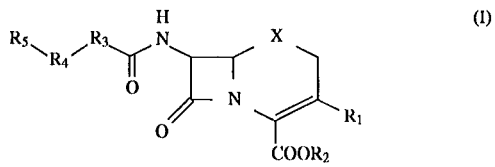

wherein
X is $CH_2$, S or O;
$R_1$ is a 3-position substituent such as hydrogen, hydroxy, halo, trifluoromethyl, $C_2F_5$, $C_1$–$C_6$ alkyl, $C_1$–$C_6$ substituted alkyl, $C_1$–$C_6$ alkenyl', $C_1$–$C_6$ alkynyl, $CH_2O(CO)R'$, $CH_2O(CO)NH_2$, $CO_2R'$, thio($C_1$–$C_6$)alkyl, thio($C_1$–$C_6$)alkenyl, oxo($C_1$–$C_6$)alkyl, phosphine oxide, quaternary ammonium group, substituted or unsubstituted thiazolothio, or oxo($C_1$–$C_6$)alkenyl, wherein R' is hydrogen, $C_1$–$C_6$ alkyl, or $C_1$–$C_6$ alkenyl;
$R_2$ is hydrogen or a carboxy protecting group;
$R_3$ is

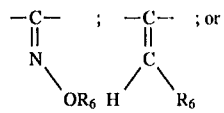

$(CH_2)_n$; wherein $R_6$ is hydrogen, $C_1$–$C_6$ alkyl, $CH_2F$, $CF_3$, $C_2H_5$, $CH_2CH_2F$, $CH_2CF_3$, $C_2F_5$, $CH_2CO_2R'$, $CH_2CONH_2$, $C(CH_2)_2CO_2R'$, or $C(CH_2)_2CONH_2$; and n is 0–5;
$R_4$ is

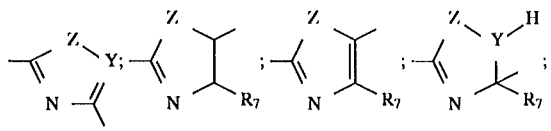

wherein Z is O, S, NH, or $CH_2$; Y is CH or N; and $R_7$ is hydrogen, $C_1$–$C_6$ alkyl, $CONH_2$, or $CO_2R'$; and
$R_5$ is

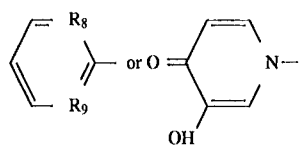

wherein $R_8$ is CH, N, COH, $COC_1$–$C_6$ alkyl, CSH, or $CNH_2$; and $R_9$ is $R_8$ as defined; said $R_5$ optionally substituted 1–4 times with halo, OH, SH, $NH_2$, $NO_2$, $CH_3$, $C_2H_5$, $CO_2R'$, $CONH_2$, $SO_3H$, or $SO_2NHR'$; and salts thereof. Also encompassed by the invention are pharmaceutical formulations using the above compounds, and methods for the treatment of infectious diseases in man and animals.

DESCRIPTION OF THE INVENTION

The β-lactams encompassed by the invention inhibit the growth of microorganisms pathogenic to man and animals and may be used to control infectious diseases.

In the above compounds, the term "3-position substituent", ($R_1$), is defined to encompass 3-position substituents in the cephalosporin, carbacephalosporin and oxacephalosporin arts. These include, but are not limited to, bromo, chloro, fluoro, iodo, hydroxy, hydrogen, trifluoromethyl, $C_2F_5$, $CH_2O(CO)R'$, $CH_2O(CO)NH_2$, $CO_2R'$, thio($C_1$–$C_6$)alkyl, thio($C_1$–$C_6$)alkenyl, oxo($C_1$–$C_6$)alkyl, oxo($C_1$–$C_6$)alkenyl, $C_1$–$C_6$ alkyl, $C_1$–$C_6$ substituted alkyl, $C_1$–$C_6$ alkenyl, $C_1$–$C_6$ substituted alkenyl, $C_1$–$C_6$ alkynyl, $C_1$–$C_6$ substituted alkynyl, $C_1$–$C_6$ alkoxy, $C_1$–$C_6$ substituted alkoxy,

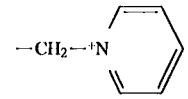

phosphine oxides, and

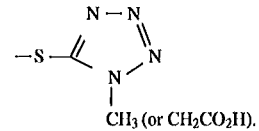

$CH_3$ (or $CH_2CO_2H$).

U.S. Pat. Nos. 5,128,336, 4,980,348, 5,084,447, and 5,077,287, and EPO Application Number 92300181.2, published Jan. 9, 1992, are all referred to for 3-position substituents, and are all hereby incorporated by reference.

$R_2$ may be a carboxy protecting group, hydrogen, or a salt thereof, all of which are well known in the art.

The term "carboxy-protecting group" as used in the specification refers to one of the ester derivatives of a carboxylic acid group commonly employed to block or protect the carboxylic acid group while reactions are carried out on other functional groups on the compound. Examples of such carboxylic-acid protecting groups include 4-nitrobenzyl, 4-methylbenzyl, 3,4-dimethoxybenzyl, 2,4-dimethoxybenzyl, 2,4,6-trimethoxybenzyl, 2,4,6-trimethylbenzyl, pentamethylbenzyl, 3,4-methylenedioxybenzyl, benzhydryl, 4,4'-dimethoxybenzhydryl, 2,2',4,4'-tetramethoxybenzhydryl, t-butyl, t-amyl, trityl, 4-methoxytrityl, 4,4'-dimethoxytrityl, 4,4',4"-trimethoxytrityl, 2-phenylprop-2-yl, trimethylsilyl, t-butyldimethylsilyl, phenacyl, 2,2,2-trichloroethyl, β-(di(n-butyl)methylsilyl)ethyl, p-toluenesulfonylethyl, 4-nitrobenzylsulfonylethyl, allyl, cinnamyl, 1-(trimethylsilylmethyl)prop-1-en-3-yl, and like moieties. The species of carboxy-protecting group employed is not critical so long as the derivatized carboxylic acid is stable to the condition of subsequent reaction(s) on other positions of the ring system and can be removed at the appropriate point without disrupting the remainder of the molecule. Similar carboxy-protecting groups used in the cephalosporin, penicillin and peptide arts can also be used to protect carboxy group substituents of the azetidinone. Further examples of these groups are found in E. Haslam, "Protective Groups in Organic Chemistry", J. G. W.

McOmie, Ed., Plenum Press, New York, N.Y., 1973, Chapter 5, and T. W. Greene, "Protective Groups in Organic Synthesis", John Wiley and Sons, New York, N.Y., 1981, Chapter 5. The related term "protected carboxy" denotes that a carboxy group is substituted with one of the above carboxy-protecting groups.

The compounds of the formula (I) may be prepared by acylating the nucleus of the formula.

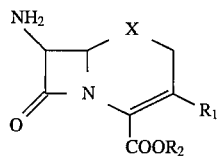

with the appropriate acyl side chain.

The acyl side-chains may be prepared by established procedures. More particularly, Schemes I–IV illustrate such procedures.

Scheme I
Phenyloxazoline Formation

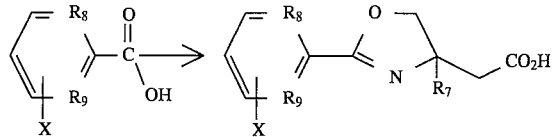

Preparation under Scheme I may be accomplished as set out in Yokokawa et al., *Synlett*, 1992, 149, or Misra et al., *Bioorg. Med. Chem. Lett.*, 1991, 1, 461.

Scheme II
Phenyloxazole Formation

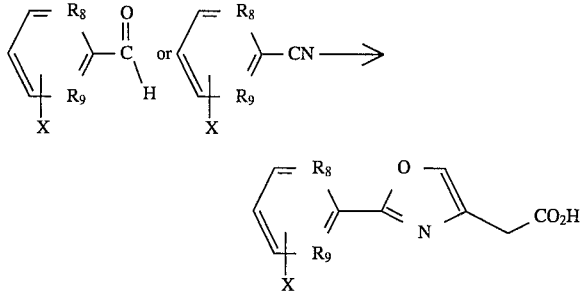

Preparation under Scheme II may be accomplished as set out in Doyle et al., *Tet. Lett.*, 1992, 33, 7769; Yoo, S.-K. *Tet. Lett.*, 1992, 2159; Connell et al., *Tet. Lett.*, 1991, 32, 17; or Goddard, C. J. *J. Heterocyclic Chem.*, 1991, 28, 17.

Scheme III
Phenyloxadiazole Formation

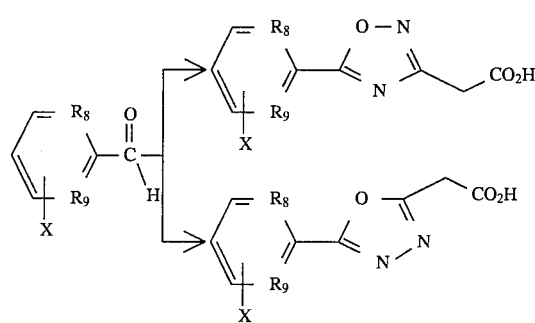

Preparation under Scheme III may be accomplished as set out in Goddard, C. J. *J. Heterocyclic Chem.*, 1991, 28, 17.

Scheme IV
Phenylthiazoline

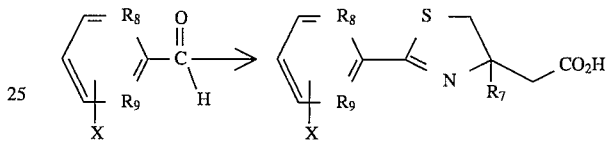

Preparation under Scheme IV may be accomplished as set out in Mulqueen et al., *Tet. Lett.*, 1993, 49, 5359.

It was envisioned that the synthesis of the target β-lactams could proceed through Morpho CDI-assisted amidation (Sheehan, et al, *J. Org. Chem*, 21, 439 (1956)), of diphenylmethyl esters with thiazoleacetic acids. The latter in turn could be synthesized following Hantzsch's thiazole synthesis methodology, (Schwarz, G. *Organic Syntheses*, Coll., Vol., II, ed. by Horning, E. C., John Wiley & Sons, Inc., New York, 1955, p.332).

As depicted in Scheme V, treatment of 3-hydroxypicolinamide 1 with Lawesson's reagent delivered thioamide 3c; whereas 3a, 3b and 3d were readily obtained from respective benzonitriles 2 after treatment with o,o-dimethyldithiophosphoric acid in the presence of water, (Yousif, N. M. *Tetrahedron* 1989, 45, 4599).

Scheme V (a)

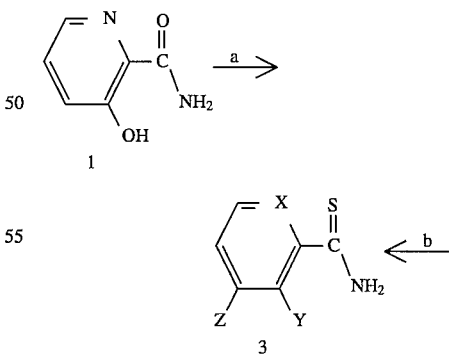

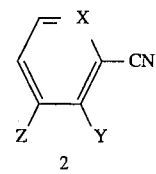

-continued
Scheme V (a)

|    | X    | Y   | Z  |
|----|------|-----|----|
| 3a | C—H  | OH  | H  |
| 3b | C—OH | OH  | H  |
| 3c | N    | OH  | H  |
| 3d | C—H  | H   | OH |

<sup>a</sup>Reagents:
(a) Ar₂P₂S₄ (Lawesson's reagent), ClCH₂CH₂Cl, reflux;
(b) (EtO)₂P(S)SH, H₂O, 60–80° C.

Following Hantzsch thiazole synthesis, thioamides 3a–d were converted to the corresponding thiazoleacetic acid ethyl esters 4a–d, (Scheme VI). The reaction rate was significantly accelerated by adding lithium bromide. Subsequent base hydrolysis of esters 4a–d afforded the thiazoleacetic acids 5a–d. Meanwhile 4a was methylated and followed by base hydrolysis to give thiazoleacetic acid 5c.

ranic acids 6a–d with diphenyldiazomethane, were acylated with thiazoleacetic acids 5a–c using Morpho CDI as an activator to provide cephalosporins 8a–o. Morpho CDI possesses reactivity comparable to DIPC (Sarantakis, D. Biochem. Biophys. Res. Commun. 1976, 78, 336) and DCC but offers the advantage of yielding a polar urea by-product which could be readily filtered off by simply passing the reaction mixture through a short pad of silica gel, the filtrate was concentrated and the acylated cephalosporins 8a–o were crystallized out from THF/CH₂Cl₂/hexane. Notably some of the cephalosporins 8a–o tended to form into a "frozen jelly" with various organic solvents, that made the aqueous extractive workup impossible and made the chromatographic separation extremely cumbersome and impractical. Cephalosporins 8a–o were de-diphenylmethylated by treating with trifluoroacetic acid at 0° C. in 1,2-dichloroethane to give the target cephalosporins 9a–o. Triethylsilane was used as a

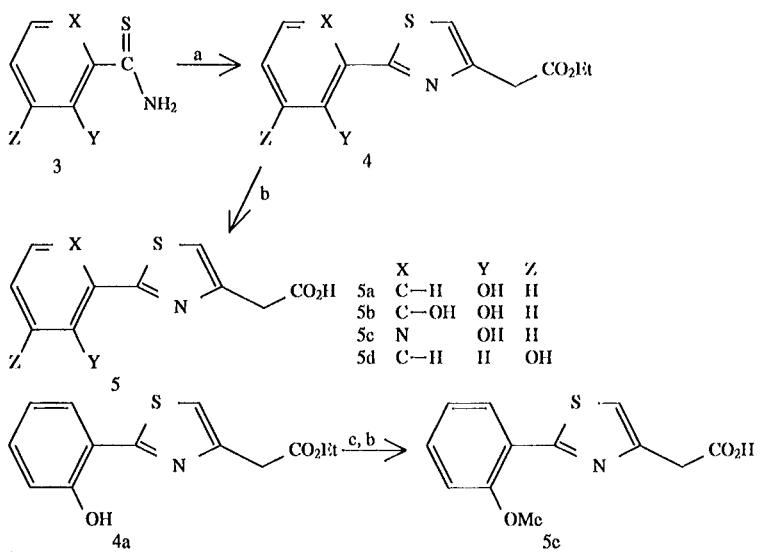

Scheme VI<sup>a</sup>

|    | X    | Y   | Z  |
|----|------|-----|----|
| 5a | C—H  | OH  | H  |
| 5b | C—OH | OH  | H  |
| 5c | N    | OH  | H  |
| 5d | C—H  | H   | OH |

<sup>a</sup>Reagents:
(a) ClCH₂C(O)CH₂CO₂Et, LiBr, THF, reflux;
(b) LiOH, THF/MeOH, rt; aq. HCl;
(c) (MeO)₂SO₂, K₂CO₃, acetone, rt.

At this juncture, as illustrated by Scheme VII, below, 7β-aminocephalosporanic acid diphenylmethyl esters 7a–d, which were derived from treatment of 7β-aminocephalospo- ranic carbonium ion scavenger.

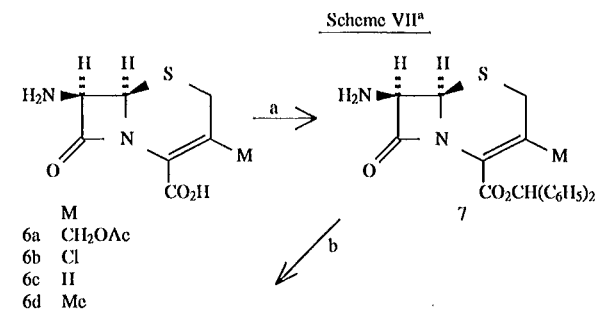

Scheme VII<sup>a</sup>

|    | M      |
|----|--------|
| 6a | CH₂OAc |
| 6b | Cl     |
| 6c | H      |
| 6d | Me     |

-continued
Scheme VII[a]

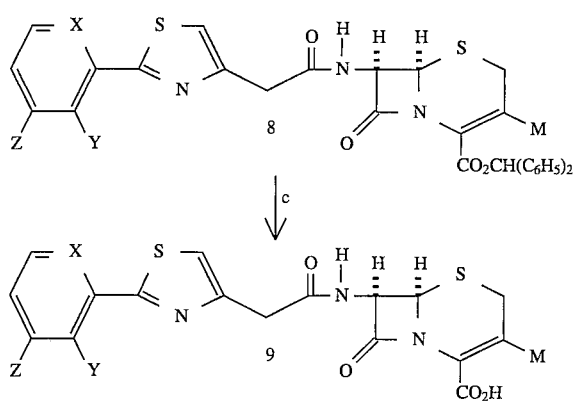

| | X | Y | Z | M | | X | Y | Z | M |
|---|---|---|---|---|---|---|---|---|---|
| 9a | C—H | OH | H | CH₂OAc | 9i | N | OH | H | CH₂OAc |
| 9b | C—H | OH | H | Cl | 9j | N | OH | H | Cl |
| 9c | C—H | OH | H | H | 9k | N | OH | H | H |
| 9d | C—H | OH | H | Me | 9l | N | OH | H | Me |
| 9e | C—OH | OH | H | CH₂OAc | 9m | C—H | H | OH | CH₂OAc |
| 9f | C—OH | OH | H | Cl | 9n | C—H | H | OH | H |
| 9g | C—OH | OH | H | H | 9o | C—H | OMe | H | CH₂OAc |
| 9h | C—OH | OH | H | Me | | | | | |

[a]Reagents:
(a) $(C_6H_5)_2CN_2$, $CH_3CN$, rt;
(b) 5a–e, Morpho CDI, THF/$CH_2Cl_2$, 0°C.;
(c) TFA, $Et_3SiH$, $ClCH_2CH_2Cl$, 0°C.

Cephalosporins 9a–o were assayed against a broad array of Gram-positive and Gram-negative bacteria in Mueller-Hinton agar by the 2-fold serial dilution method, (Kirst, H. A.; *J. Antibiot.* 1982, 35, 1675). Cefotaxime, a "third-generation" cephalosporin, was co-assayed as a standard; vancomycin, which is a linear glycoheptapeptide and has potent activity only against the Gram-positive bacteria including methicillin-resistant staphylococci, was also co-assayed for comparison purpose. As a result, cephalosporins 9a–o distinctively displayed activity against the Gram-positive bacteria, but not the Gram-negative bacteria. Moreover, as indicated in Table I, the ones with acetyloxymethyl at the 3-position, 9a, 9i, 9e, 9o, and 9m, exhibited activity with minimal inhibitory concentrations (MICs) of 16 μg/mL or lower against 4 strains of methicillin-resistant staphylococci, namely *Staphylococcus aureus* X400 and S13E and *Staphylococcus epidermidis* 270 and 222.

Determination of Minimal Inhibitory Concentrations (MIC)

Test compounds were diluted to an appropriate range of concentrations in 0.1M phosphate buffer (pH 7), incorporated into Mueller-Hinton agar (difco) supplemented with 1% Bacto-Supplement C (Difco) at 50° C. and allowed to solidify in petri dishes. Fresh overnight cultures of test bacteria were diluted to approximately $1\times10^4$ cells/mL aand applied in 1-mL volumes to the surface of the agar plates. The inoculated plates were incubated overnight at 35° C. in ambient air. MIC endpoints were recorded as the lowest antibiotic concentrations that inhibited the development of visible bacterial growth on the plates.

TABLE I

| | In vitro activity (MIC[a], μg/mL) of cephalosporins | | | | | | | |
|---|---|---|---|---|---|---|---|---|
| Organisms | 9a | 9i | 9e | 9o | 9m | 9f | Cefot[b] | Vanc[c] |
| Gram-positive bacteria | | | | | | | | |
| Staph. aureus (X1.1) | 0.03 | 0.125 | 8.0 | 0.06 | 0.25 | 16 | 1.0 | 0.5 |
| Staph. aureus (V41) | 0.25 | 0.5 | 16 | 0.5 | 1.0 | 16 | 2.0 | 0.5 |
| Staph. aureus (X400)[d] | 2.0 | 4.0 | 16 | 16 | 16 | 16 | 128 | 0.5 |
| Staph. aureus (S13E)[d] | 2.0 | 2.0 | 4.0 | 8.0 | 8.0 | 16 | 64 | 0.5 |
| Staph. epiderm. (270)[d] | 0.125 | 0.5 | 4.0 | 0.5 | 1.0 | 8.0 | 8.0 | NT[f] |
| Staph. epiderm. (222)[d] | 4.0 | 0.125 | 0.5 | 0.125 | 0.25 | 2.0 | 2.0 | 0.5 |
| Strept. pyogenes (C203) | 1.0 | 0.015 | 0.03 | 0.015 | NT | 0.06 | 0.008 | 0.5 |
| Enter. faecium (X66) | 16 | 8.0 | 4.0 | 16 | 32 | 8.0 | 128 | 0.5 |
| Enter. faecalis (2041) | 2.0 | 8.0 | 4.0 | 8.0 | 16 | 8.0 | 1.0 | 2.0 |
| Gram-negative bacteria | | | | | | | | |
| H. influenzae (C.L.) | 8.0 | 4.0 | 4.0 | 64 | NT | 1.0 | 0.008 | 64 |

TABLE I-continued

| | In vitro activity (MIC[a], μg/mL) of cephalosporins | | | | | | | |
|---|---|---|---|---|---|---|---|---|
| Organisms | 9a | 9i | 9c | 9o | 9m | 9f | Cefot[b] | Vanc[c] |
| H. influenzae (76) | 0.5 | 2.0 | 4.0 | 4.0 | NT | 1.0 | 0.008 | 128 |
| E. coli (N10) | 128 | 128 | 64 | 128 | 128 | 32 | 0.06 | 128 |
| E. coli (EC14) | 128 | 128 | 16 | 128 | 128 | 32 | 0.015 | 128 |
| E. coli (TEM) | 128 | 128 | 64 | 128 | 128 | 32 | 0.008 | 128 |
| K. pneumonia (X26) | 2.0 | 1.0 | 0.5 | 2.0 | 4.0 | 0.5 | 0.008 | 128 |
| K. pneumonia (KAE) | 128 | 128 | 128 | 128 | 128 | 128 | 1.0 | 128 |
| K. pneumonia (X68) | 128 | 128 | 16 | 128 | 128 | 32 | 0.015 | 128 |
| other Gram(−) bacteria[e] | >64 | >64 | >64 | >64 | >64 | >64 | . . | 128 |

[a]MIC: Minimal inhibitory activity. Agar dilution method was used.
[b]Cefot: Cefotaxime. Which was used as a standard.
[c]Vanc: Vancomycin.
[d]Methicillin-resistant strain.
[e]Other Gram-negative bacteria included in the test were *Enterobacter aerogenes* (C32 and EB17), *Enterobacter cloacae* (EB5 and 265A), *Salmonella typhi* (X514), *Salmonella typhimurium* (1335), *Pseudomonas aeruginosa* (X528, X238, PS18, and PS72), *Serratia marcescens* (X99 and SE3), *Shigella sonnei* (N9), *Morganella morganii* (PR15), *Providencia stuartii* (PR33), *Providencia rettgeri* (C24), *Citrobacter freundii* (CF17), and *Acinetobacter calcoaceticus* (AC12).
[f]NT: Not tested.

It is known that resistance to methicillin in staphylococci is often of the heterogeneous type and therefore not easily detected. Detection of this resistance is greatly improved by increasing the osmolality of the medium with 2–5% NaCl and by incubating at 30°–35° C. (Goldstein, F. W.; Acar, J. J. *Antimicrob. Chemother.* 199, 27, 549). Two most active cephalosporins 9a and 9i, alongside with cefamandole and oxacillin, were subject to tests against 33 clinical isolates of methicillin-resistant staphylococci in Mueller-Hinton agar supplemented with 4% NaCl and incubated at 35° C. Although cefamandole is among the most active β-lactam antibiotics against methicillin-resistant staphylococci (Frongillo, R. F.; Bianchi, P.; Moretti, A.; Pasticci, M. D. Ripa, S.; Pauluzi, S. *Antimicrob. Agents Chemother* 1984, 25, 666), and has been successfully used clinically for the treatment of infections caused by methicillin-resistant staphylococci, (Frongillo, R. F.; Donati, L.; Federico, G.; Martino, P.; Moroni, M.; Ortnan, L.; Palumbo, M.; Pasticci, B. M.; Pizzigallo, E.; Privitera, G.; Serra, P.; Signorimi, M.; Venditti, M.; Pauluzzi, S. *Antimicrob. Agents Chemother.* 1986, 29, 789), it showed poorer efficacy than vancomycin in animal models, (Chambers, H. F.; Hackbarth, C. J.; Drake T. A.; Rusnak, M. G.; Sande, M. A. J. *Infect. Dis.* 1984, 149, 894). The geometric mean MIC of oxacillin rose from 49 to 97 μg/mL with the addition of NaCl; whereas MICs of 9a and 9i were only slightly elevated in the presence of NaCl, and remained in the range usually considered to be clinically achievable concentrations for cephalosporins (Table II).

TABLE II

Geometric mean MICs (μg/mL) of 9a and 9i tested against 33 strains of methicillin-resistant staphylococci

| Media | 9a | 9i | Cefamandole[a] | Oxacillin[b] |
|---|---|---|---|---|
| MHA[c] | 1.7 | 4.8 | 6.8 | 49 |
| MHA + 4% NaCl[d] | 2.4 | 8.0 | 13 | 97 |

[a]A "second-generation" cephalosporin.[16-18]
[b]A clinically used penicillin, which was used as a control in the test.
[c]Mueller-Hinton agar.
[d]MHA supplemented with 4% NaCl was used to improve the detection of methicillin resistance in staphylococci.

This invention also provides a method for treating infectious diseases in man and other animals and pharmaceutical formulations suitable for administration in the treatment method. The therapeutic mehtod of this invention comprises administering to man or other animals an antibiotically effective non-toxic dose of a compound represented by Formula (1) or a pharmaceutically acceptable salt thereof.

An antibiotically effective amount is an amount between about 25 mg and about 2 grams. The compound, salt or ester may be administered in a single dose or in multiple doses throughout the day. Treatment may continue for a week to ten days or longer deepending upon the duration of the infection. The particular dose and regimen can depend on such factors as the weight and age of the patient, the particular causative organism, the severity of the infection, the general health of the patient, and the tolerance of the individual to the antibiotic.

The compound may be administered parenterally, subcutaneously or rectally. As with other β-lactam antibiotics, the method of this invention may be used prophylactically to prevent infections after exposure or before possible exposure, e.g., preoperatively. The antibiotic may be administered by conventional methods, e.g., by syringe or by intravenous drip.

The pharmaceutically-acceptable salts as noted above can be useful forms of the antibiotics for preparing antibiotic formulations.

The pharmaceutical formulations of the invention comprise an antibiotically effective non-toxic amount of a compound represented by Formula (1) or a pharmaceutically acceptable non-toxic salt thereof, and a pharmaceutically acceptable carrier.

Parenteral formulations of the antibacterial agent for injection are formulated with Water-for-Injection, Ringer's solution, physiological saline or glucose solution. The antibiotic also may be administered in an intravenous fluid by the drip method.

For parenteral use the antibacterial agent of Formula (1) or a pharmaceutically acceptable salt thereof, can be made up preferably in dry crystalline powder form or as a lyophilized powder and filled into vials. Such vials may contain between about 100 mg and about 2 grams of antibiotic per vial.

EXPERIMENTAL SECTION

General Remarks

Reagents were used as supplied unless otherwise noted. Reactions were run under dry nitrogen or argon atmosphere unless otherwise noted. Silica gel (E. Merck, 230–400 mesh ASTM) was used for flash column chromatography. LiChroprep RP-18 (E. Merck, 40–63 μm) was used for reverse phase column chromatography. $^1$H NMR spectra were recorded on a General Electric QE-300 instrument. Infrared (IR) spectra were determined on a Nicolet MX-1 FT-IR. Mass spectral data (MS) were obtained on either a Varian MAT-731 (for FDMS) or a Zab 3F-VG (for FABMS and HRMS) spectrometer. Melting points are uncorrected.

EXAMPLE 1

3-Hydroxy-2-pyridinecarbothioamide (3c)

A stirred solution of 3-hydroxypicolinamide (1.35 g, 9.75 mmol) and Lawesson's reagent (2.37 g, 5.85 mmol) in dry ClCH$_2$CH$_2$Cl (12 mL) was heated to reflux under nitrogen for 5 hr. At ambient temperature, the mixture was diluted with EtOAc (50 mL), washed with half-saturated aq. NaCl (30 mL) containing NaHCO$_3$ (840 mg) and with brine (20 mL). After drying over MgSO$_4$ and filtration, the filtrate was concentrated in vacuo to give a brown solid, which was subject to flash chromatography on silica gel (CH$_2$Cl$_2$ as eluent) to provide 3c (623 mg, 42%) as a greenish yellow solid after crystallization from EtOAc/hexane. mp 152.0–153.0° C.; IR (KBr) 3372, 3259, 2464, 1626, 1458, 1317 cm$^{-1}$; $^1$H NMR (DMSO-d$_6$) δ7.33 (1H, dd, J=8.6 and 1.0 Hz, Ar), 7.46 (1H, dd, J=8.6 and 4.3 Hz, Ar), 8.07–8.10 (1H, m, Ar), 8.15(1H, s, NH), 8.49 (1H, s, NH), 12.76 (1H, s, OH); FABMS m/z 154 (M$_+$); Anal. Calcd for C$_6$H$_6$N$_2$OS: C, 46.74; H, 3.92; N, 18.17. Found: C, 46.83; H, 3.89; N, 17.90.

EXAMPLE 2

2-Hydroxybenzenecarbothioamide (3a)

A stirred solution of 2-hydroxybenzonitrile (23.8 g, 200 mmol), (EtO)$_2$P(S)SH (33.6 mL, 200 mmol) and water (40 mL) was heated at 80° C. for 12 hr under nitrogen. The mixture was cooled down to 0°–10° C., diluted with CH$_2$Cl$_2$ (200 mL)/Et$_2$O (400 mL), then cautiously treated with saturated aq. NaHCO$_3$ (60 mL), and followed by adding solid NaHCO$_3$ in small portions until CO$_2$ evolution ceased. Half-saturated aq. NaCl (40 mL) was added to the mixture. The organic layer was separated, washed with brine (100 mL), dried over MgSO$_4$, and filtered. After concentration in vacuo, the residue was chromatographed on silica gel (gradient EtOAc/CH$_2$Cl$_2$: 0–5%) to give 3a (16.7 g, 55%) as a pinkish solid, which had the same $^1$H NMR data as reported in the literature (Yousif, N. M. *Tetrahedron* 1989, 45, 4599).

EXAMPLE 3

2,6-Dihydroxybenzenecarbothioamide (3b)

The procedure used for the preparation of 3a was repeated with 2,6-dihydroxybenzonitrile (8.75 g, 64.8 mmol), (EtO)$_2$P(S)SH (32.6 mL, 194 mmol) and water (26 mL) at 60° C. for 36 hr to give 3b (4.76 g, 43%) as a light yellow solid after chromatographic purification on silica gel (gradient EtOAc/CH$_2$Cl$_2$: 0–5%) and crystallization from EtOAc/hexane. mp 180° C. (dec); IR (KBr) 3411, 3295, 3177, 2380, 1612, 1577, 1464, 1267, 1010 cm$^{-1}$; $^1$H NMR (DMSO-d$_6$) δ 6.31 (2H, d, J=8.1 Hz, Ar), 7.00 (1H, t, J=8.1 Hz, Ar), 9.60 (1H, br s, NH), 9.96 (1H, br s, NH), 10.93 (2H, s, OH); FABMS m/z 169 (M$_+$), 170 (M$^+$+1); Anal. Calcd for C$_7$H$_7$NO$_2$S: C, 49.69; H, 4.17; N, 8.28. Found: C, 49.89; H, 4.23; N, 8.36.

EXAMPLE 4

3-Hydroxybenzenecarbothioamide (3d)

The procedure used for the preparation of 3a was repeated with 3-hydroxybenzonitrile (5.48 g, 46.1 mmol), (EtO)$_2$P(S)SH (7.72 mL, 46.1 mmol) and water (9.2 mL) at 80° C. for 36 hr to give 3d (4.04 g, 57%) as a yellow solid after chromatographic purification on silica gel (gradient EtOAc/CH$_2$Cl$_2$: 6–12%) and crystallization from EtOAc/hexane. mp 139.0°–140.0° C.; IR (KBr) 3340, 3280, 3165, 1629, 1590, 1462 cm$^{-1}$; $^1$H NMR (DMSO-d$_6$) δ6.83 (1H, br d, J=7.0 Hz, Ar), 7.10–7.25 (2H, m, Ar), 7.27 (1H, s, Ar), 9.33 (1H, br s, NH), 9.58 (1H, s, OH), 9.72 (1H, br s, NH); FDMS m/z 153 (M$^+$); Anal. Calcd for C$_7$H$_7$NOS: C, 54.88; H, 4.60; N, 9.14. Found: C, 55.01; H, 4.53; N, 9.02.

EXAMPLE 5

2-(2-Hydroxyphenyl)-4-thiazoleacetic Acid Ethyl Ester (4a)

A stirred solution of 2-hydroxybenzenecarbothioamide 3a (5.36 g, 35.0 mmol), ethyl 4-chloroacetoacetate (6.34 g, 38.5 mmol) in dry THF (70 mL) was heated to reflux under nitrogen for 2.5 days. At ambient temperature, the mixture was diluted with EtOAc (200 mL), then cautiously treated with saturated aq. NaHCO$_3$ (40 mL), and followed by adding solid NaHCO$_3$ in small portions until CO$_2$ evolution ceased. The organic layer was separated, washed with brine (40 mL×2), dried over MgSO$_4$, and filtered. After concentration in vacuo, the oily residue was chromatographed on silica gel (gradient EtOAc/CH$_2$Cl$_2$: 0–4%) to provide 4a (8.53 g, 93%) as a white solid, which was recrystallized from toluene/hexane at −30° C. mp 35.5°–36.5° C.; IR (neat) 3120, 1740, 1480, 1225 cm$^{-1}$; $^1$H NMR (DMSO-d$_6$) δ1.15 (3H, t, J=7.1 Hz, CH$_3$), 3.84 (2H, s, CH$_2$), 4.07 (2H, q, J=7.1 Hz, CH$_2$), 6.89 (1H, t, J=7.8 Hz, Ar), 6.97 (1H, d, J=7.8 Hz, Ar), 7.26 (1H, t, J=7.8 Hz, Ar), 7.48 (1H, s), 7.93 (1H, d, J=7.8 Hz, Ar), 11.29 (1H, s, OH); FABMS m/z 263 (M$_+$), 264 (M$^+$+1); Anal. Calcd for C$_{13}$H$_{13}$NO$_3$S: C, 59.30; H, 4.98; N, 5.32. Found: C, 59.16; H, 4.97; N, 5.50.

EXAMPLE 6

2-(2,6-Dihydroxyphenyl)-4-thiazoleacetic Acid Ethyl Ester (4b)

The procedure used for the preparation of 4a was repeated with 2,6-dihydroxybenzenecarbothioamide 3b (1.02 g, 6.04 mmol), ethyl 4-chloroacetoacetate (1.99 g, 12.1 mmol), and LiBr (525 mg, 6.04 mmol) in dry THF (15 mL) to give 4b (1.16 g, 69%) as a white solid after chromatographic purification on silica gel (gradient EtOAc/CH$_2$Cl$_2$: 0–12%) and recrystallization from EtOAc/hexane. mp 152.5°–154.0° C.; IR (KBr) 3256 (br), 1742, 1460, 1157 cm$^{-1}$; $^1$H NMR (DMSO-d$_6$) δ1.17 (3H, t, J=7.2 Hz, CH$_3$), 3.88 (2H, s, CH$_2$), 4.08 (2H, q, J=7.2 Hz, CH$_2$), 6.44 (2H, d, J=8.2 Hz, Ar), 7.09 (1H, t, J=8.2 Hz, Ar), 7.51 (1H, s), 12.19 (2H, s, OH); FDMS m/z 279 (M$_+$); Anal. Calcd for C$_{13}$H$_{13}$NO$_4$S: C, 55.90; H, 4.69; N, 5.01. Found: C, 56.19; H, 4.85; N, 4.86.

EXAMPLE 7

2-(3-Hydroxy-2-pyridinyl)-4-thiazoleacetic Acid Ethyl Ester (4c)

The procedure used for the preparation of 4a was repeated with 3-hydroxy-2-pyridinecarbothioamide 3c (358 mg, 2.32 mmol), ethyl 4-chloroacetoacetate (0.628 mL, 4.65 mmol), and LiBr (202 mg, 2.32 mmol) in dry THF (6 mL) to give 4c (552 mg, 90%) as a white solid after chromatographic purification on silica gel (gradient EtOAc/CH$_2$Cl$_2$: 0–12%) and recrystallization from CH$_2$Cl$_2$/hexane. mp 85.5°–86.5° C.; IR (KBr) 3400, 1723, 1436, 1202, 1178 cm$^{-1}$; $^1$H NMR (DMSO-d$_6$) δ1.16 (3H, t, J=7.1 Hz, CH$_3$), 3.93 (2H, s, CH$_2$), 4.08 (2H, q, J=7.1 Hz, CH$_2$), 7.37 (1H, dd, J=8.3 and 4.2 Hz, Ar), 7.45 (1H, d, J=8.3 Hz, Ar), 7.66 (1H, s), 8.15 (1H, d, J=4.2 Hz, Ar), 11.64 (1H, s, OH); FDMS m/z 264 (M$_+$); Anal. Calcd for C$_{12}$H$_{12}$N$_2$O$_3$S: C, 54.53; H, 4.58; N, 10.60. Found: C, 54.83; H, 4.66; N, 10.30.

EXAMPLE 8

2-(3-Hydroxyphenyl)-4-thiazoleacetic Acid Ethyl Ester (4d)

The procedure used for the preparation of 4a was repeated with 3-hydroxybenzenecarbothioamide 3d (1.53 g, 10.0 mmol) and ethyl 4-chloroacetoacetate (1.65 g, 10.0 mmol) in dry THF (20 mL) to give 4d (2.04 g, 78%) as a white solid after chromatographic purification on silica gel (gradient EtOAc/hexane: 30–40%) and recrystallization from EtOAc/hexane. mp 95.5°–97.2° C.; IR (KBr) 3112, 1727, 1278 cm$^{-1}$; $^1$H NMR (DMSO-d$_6$) δ1.15 (3H, t, J=7.0 Hz, CH$_3$), 3.81 (2H, s, CH$_2$), 4.07 (2H, q, J=7.0 Hz, CH$_2$), 6.81 (1H, d, J=7.3 Hz, Ar), 7.22–7.30 (3H, m, Ar), 7.46 (1H, s), 9.68 (1H, s, OH); FDMS m/z 263 (M$_+$); Anal. Calcd for C$_{13}$H$_{13}$NO$_3$S: C, 59.30; H, 4.98; N, 5.32. Found: C, 59.41; H, 4.91; N, 5.30.

EXAMPLE 9

2-(2-Hydroxyphenyl)-4-thiazoleacetic Acid (5a)

A stirred solution of 4a (824 mg, 3.13 mmol) in THF (5 mL)/MeOH (5 mL) was treated with 2N LiOH (4 mL), the resultant mixture was stirred at ambient temperature under nitrogen for 30 min. The mixture was treated with 5N HCl (2 mL), followed by adding EtOAc (50 mL) and solid NaCl to saturate the aq. layer. The organic layer was separated, washed with brine (20 mL×2), dried over MgSO$_4$, filtered, and concentrated in vacuo to give a solid residue. After recrystallization from acetone/hexane, 5a (730 mg, 99%) was obtained as a white solid. mp 173.0°–174.0° C.; IR (KBr) 3250–2400 (br), 3108, 1696, 1223 cm$^{-1}$; $^1$H NMR (DMSO-d$_6$) δ3.76 (2H, s, CH$_2$), 6.89 (1H, t, J=7.8 Hz, Ar), 6.96 (1H, d, J=7.8 Hz, Ar), 7.26 (1H, t, J=7.8 Hz, Ar), 7.45 (1H, s), 7.92 (1H, d, J=7.8 Hz, Ar), 11.33 (1H, s, OH), 12.42 (1H, br s, CO$_2$H); FABMS m/z 235 (M$_+$), 236 (M$^+$+1); Anal. Calcd for C$_{11}$H$_9$NO$_3$S: C, 56.16; H, 3.86; N, 5.95. Found: C, 56.30; H, 3.85; N, 6.10.

EXAMPLE 10

2-(2,6-Dihydroxyphenyl)-4-thiazoleacetic Acid (5b)

The procedure used for the preparation of 5a was repeated with 4b (805 mg, 2.89 mmol) and 2N LiOH (5.1 mL) to provide 5b (680 mg, 94%) as a yellowish solid, which was recrystallized from THF/hexane. mp 210° C. (dec); IR (KBr) 3540–2500 (br), 3256 (br), 1688, 1461, 1230 cm$^{-1}$; $^1$H NMR (DMSO-d$_6$) δ3.78 (2H, s, CH$_2$), 6.42 (2H, d, J=8.1 Hz, Ar), 7.08 (1H, t, J=8.1 Hz, Ar), 7.46 (1H, s), 12.21 (2H, s, OH), 12.47 (1H, br s, CO$_2$H); FDMS m/z 251 (M$_+$), 252 (M$^+$+1); Anal. Calcd for C$_{11}$H$_9$NO$_4$S: C, 52.58; H, 3.61; N, 5.57. Found: C, 52.36; H, 3.57; N, 5.38.

EXAMPLE 11

2-(3-Hydroxy-2-pyridinyl)-4-thiazoleacetic Acid (5c)

The procedure used for the preparation of 5a was repeated with 4c (335 mg, 1.27 mmol) and 2N LiOH (2.22 mL) to provide 5c (296 mg, 99%) as a white solid, which was recrystallized from EtOAc/hexane. mp 175.0°–176.0° C.; IR (KBr) 3450, 3300–2500 (br), 1729, 1697, 1449, 1189 cm$^{-1}$; $^1$H NMR (DMSO-d$_6$) δ3.83 (2H, s, CH$_2$), 7.37 (1H, dd, J=8.5 and 4.4 Hz, Ar), 7.44 (1H, d, J=8.5 Hz, Ar), 7.63 (1H, s), 8.14 (1H, d, J=4.4 Hz, Ar), 11.70 (1H, s, OH), 12.54 (1H, s, CO$_2$H); FDMS m/z 237 (M$^+$+1); Anal. Calcd for C$_{10}$H$_8$N$_2$O$_3$S: C, 50.84; H, 3.41; N, 11.86. Found: C, 50.77; H, 3.42; N, 11.74.

EXAMPLE 12

2-(3-Hydroxyphenyl)-4-thiazoleacetic Acid (5d)

The procedure used for the preparation of 5a was repeated with 4d (1.84 g, 7.00 mmol) and 2N LiOH (14.0 mL) to provide 5d (1.63 g, 99%) as a white solid, which was recrystallized from EtOAc/toluene. mp 172.0°–174.0° C.; IR (KBr) 3500–2400 (br), 3336 (br), 1689, 1442, 1276, 1231 cm$^{-1}$; $^1$H NMR (DMSO-d$_6$) δ3.72 (2H, s, CH$_2$), 6.81 (1H, d, J=7.4 Hz, Ar), 7.19–7.30 (3H, m, Ar), 7.43 (1H, s), 9.67 (1H, br s, OH), 12.40 (1H, br s, CO$_2$H); FDMS m/z 236 (M$^+$+1); Anal. Calcd for C$_{11}$H$_9$NO$_3$S: C, 56.14; H, 3.86; N, 5.95. Found: C, 56.11; H, 3.73; N, 5.80.

EXAMPLE 13

2-(2-Methoxyphenyl)-4-thiazoleacetic Acid (5e)

Dimethyl sulfate (0.133 mL, 1.41 mmol) was added to a stirred suspension of 4a (336 mg, 1.28 mmol) and K$_2$CO$_3$ (265 mg, 1.92 mmol) in dry acetone (5 mL), the resultant suspension was stirred at ambient temperature under nitrogen for 22 hr. After usual extractive workup with EtOAc (30 mL), desired methyl ether (354 mg, 100%) was obtained as a colorless oil.

The above oil was dissolved in THF (4 mL)/EtOH (4 mL) and treated with 2N LiOH (2.2 mL). The mixture was stirred at ambient temperature for 30 min before it was treated with 5N HCl (1 mL). After usual extractive workup with EtOAc (30 mL), 5c (272 mg, 85%) was obtained as a white solid, which was recrystallized from EtOAc/hexane. mp 103.5°–105.0° C.; IR (KBr) 3450 (br), 3200–2600 (br), 1722, 1198 cm$^{-1}$; $^1$H NMR (DMSO-d$_6$) δ3.74 (2H, s, CH$_2$), 3.95 (3H, s, CH$_3$), 7.04 (1H, t, J=7.7 Hz, Ar), 7.19 (1H, d, J=8.4 Hz, Ar), 7.36–7.43 (1H, m, Ar), 7.45 (1H, s), 8.18 (1H, d, J=7.7 Hz, Ar), 12.36 (1H, s, CO$_2$H); FDMS m/z 249 (M$_+$), 250 (M$^+$+1); Anal. Calcd for C$_{12}$H$_{11}$NO$_3$S: C, 57.82; H, 4.45; N, 5.62. Found: C, 57.67; H, 4.48; N, 5.62.

EXAMPLE 14

[6R-[6A,7B(R*)]]-3-[(Acetyloxy)methyl]-7-[[[2-(2-hydroxyphenyl)-4-thiazolyl]acetyl]amino]-8-oxo-5-thia-1-azabicyclo[4.2.0]oct-2-ene-2-carboxylic Acid Diphenylmethyl Ester (8a)

To a stirred solution of 7a (438 mg, 1.00 mmol) and 5a (247 mg, 1.05 mmol) in dry THF (10 mL) at 0° C. under nitrogen was added a solution of 1-cyclohexyl-3-(2-morpholinoethyl)carbodiimide metho-p-toluenesulfonate (Morpho CDI; 551 mg, 1.30 mmol) in dry $CH_2Cl_2$ (10 mL). The resultant mixture was stirred at 0° C. for 24 hr and at ambient temperature for 5 hr. The mixture was filtered through a short pad of silica gel (80% EtOAc/hexane), the filtrate was concentrated in vacuo to give a solid residue, which was recrystallized from $THF/Et_2O$ to provide 8a (507 mg, 77%) as a white solid. mp 195° C. (dec); IR (KBr) 3292, 1781, 1741, 1729, 1661., 1233 $cm^{-1}$; $^1H$ NMR (DMSO-$d_6$) δ1.91 (3H, s, $CH_3$), 3.50 (1H, d, J=18.1 Hz), 3.63 (1H, d, J=18.1 Hz), 3.75 (2H, s, $CH_2$), 4.59 (1H, d, J=12.8 Hz), 4.82 (1H, d, J=12.8 Hz), 5.13 (1H, d, J=4.8 Hz), 5.79 (1H, dd, J=8.1 and 4.8 Hz), 6.88 (1H, t, J=7.8 Hz), 6.89 (1H, s), 6.96 (1H, d, J=7.8 Hz), 7.20–7.46 (12H, m), 7.95 (1H, d, J=7.8 Hz), 9.14 (1H, d, J=8.1 Hz, NH), 11.30 (1H, s, OH); FDMS m/z 656 ($M^+$+1); Anal. Calcd for $C_{34}H_{29}N_3O_7S_2$: C, 62.28; H, 4.46; N, 6.41. Found: C, 62.04; H, 4.64; N, 6.18.

EXAMPLE 15

[6R-[6A,7B(R*)]]-3-Chloro-7-[[[2-(2-hydroxyphenyl)-4-thiazolyl]acetyl]amino]-8-oxo-5-thia-1-azabicyclo[4.2.0]oct-2-ene-2-carboxylic Acid Diphenylmethyl Ester (8b)

The procedure used for the preparation of 8a was repeated with 7b (223 mg, 0.557 mmol) and 5a (137 mg, 0.583 mmol), and Morpho CDI (247 mg, 0.583 mmol). After filtration through a short pad of silica gel (30% EtOAc/$CH_2Cl_2$), the filtrate was concentrated in vacuo to give a solid residue 8b (390 mg), which was contaminated with ca 15% of inseparable $\Delta_2$ isomer and, without further purification, was subject to de-benzhydrylation (see the formation of 9b).

EXAMPLE 16

[6R-[6A,7B(R*)]]-7-[[[2-(2-Hydroxyphenyl)-4-thiazolyl]acetyl]amino]-8-oxo-5-thia-1-azabicyclo[4.2.0]oct-2-ene-2-carboxylic Acid Diphenylmethyl Ester (8c)

The procedure used for the preparation of 8a was repeated with 7c (317 mg, 0.867 mmol) and 5a (214 mg, 0.911 mmol), and Morpho CDI (441 mg, 1.04 mmol). After filtration through a short pad of silica gel (80% EtOAc/hexane), the filtrate was concentrated in vacuo and the residue was crystallized from THF/hexane to provide 8c (348 mg, 69%) as a white solid. mp 229° C. (dec); IR (KBr) 3296 (br), 1773, 1727, 1658, 1249 $cm^{-1}$; $^1H$ NMR (DMSO-$d_6$) δ3.56 (1H, dd, J=19.2 and 6.0 Hz), 3.65 (1H, dd, J=19.2 and 2.8 Hz), 3.76 (2H, s, $CH_2$), 5.07 (1H, d, J=5.0 Hz), 5.81 (1H, dd, J=8.3 and 5.0 Hz), 6.73 (1H, dd, J=6.0 and 2.8 Hz), 6.87 (1H, s), 6.89 (1H, t, J=7.9 Hz), 6.96 (1H, d, J=7.9 Hz), 7.18–7.53 (11H, m), 7.42 (1H, s), 7.95 (1H, d, J=7.9 Hz), 9.13 (1H, d, J=8.3 Hz, NH), 11.31 (1H, s, OH); FABMS m/z 584 ($M^+$+1); Anal. Calcd for $C_{31}H_{25}N_3O_5S_2$: C, 63.79; H, 4.32; N, 7.20. Found: C, 63.61; H, 4.25; N, 6.99.

EXAMPLE 17

[6R-[6A,7B(R*)]]-7-[[[2-(2-Hydroxyphenyl)-4thiazolyl]acetyl]amino]-3-methyl-8-oxo-5-thia-1-azabicyclo[4.2.0]oct-2-ene-2-carboxylic Acid Diphenylmethyl Ester (8d)

The procedure used for the preparation of 8a was repeated with 7d (118 mg, 0.502 mmol) and 5a (190 mg, 0.500 mmol), and Morpho CDI (212 mg, 0.500 mmol). After filtration through a short pad of silica gel (30% EtOAc/$CH_2Cl_2$), the filtrate was concentrated in vacuo to give crude 8d (50 mg), which readily formed into a gelatinous solution with various solvents and was difficult to purify; therefore, it was subject to further debenzhydrylation (see the formation of 9d).

EXAMPLE 18

[6R-[6A,7B(R*)]]-3-[(Acetyloxy)methyl]-7-[[[2-(2,6-dihydroxyphenyl)-4-thiazolyl]acetyl]amino]-8-oxo-5-thia-1-azabicyclo[4.2.0]oct-2-ene-2-carboxylic Acid Diphenylmethyl Ester (8e)

The procedure used for the preparation of 8a was repeated with 7a (219 mg, 0.500 mmol) and 5b (132 mg, 0.525 mmol), and Morpho CDI (275 mg, 0.650 mmol). After filtration through a short pad of silica gel (80% EtOAc/hexane), the filtrate was concentrated in vacuo and subject to chromatographic purification on silica gel (gradient EtOAc/hexane: 60–80%) to give 8e (220 mg, 66%) as a white solid, which was recrystallized from EtOAc/hexane. mp 144.0°–145.5° C.; IR (KBr) 3288 (br), 1787, 1723, 1663, 1463, 1233 $cm^{-1}$; $^1H$ NMR (DMSO-$d_6$) δ1.91 (3H, s, $CH_3$), 3.49 (1H, d, J=18.2 Hz), 3.62 (1H, d, J=18.2 Hz), 3.77 (2H, s, $CH_2$), 4.59 (1H, d, J=13.0 Hz), 4.82 (1H, d, J=13.0 Hz), 5.12 (1H, d, J=5.0 Hz), 5.77 (1H, dd, J=8.3 and 5.0 Hz), 6.43 (2H, d, J=8.2 Hz), 6.88 (1H, s), 7.08 (1H, t, J=8.2 Hz), 7.20–7.49 (10H, m), 7.42 (1H, s), 9.16 (1H, d, J=8.3 Hz, NH), 12.18 (2H, br s, OH); FDMS m/z 671 ($M_+$); Anal. Calcd for $C_{34}H_{29}N_3O_8S_2$: C, 60.79; H, 4.35; N, 6.25. Found: C, 61.02; H, 4.56; N, 5.96.

EXAMPLE 19

[6R-[6A,7B(R*)]]-3-Chloro-7-[[[2-(2,6-dihydroxyphenyl)-4-thiazolyl]acetyl]amino]-8-oxo-5-thia-1-azabicyclo[4.2.0]oct-2-end-2-carboxylic Acid Diphenylmethyl Ester (8f)

The procedure used for the preparation of 8a was repeated with 7b (200 mg, 0.500 mmol) and 5b (123 mg, 0.490 mmol), and Morpho CDI (275 mg, 0.650 mmol). After filtration through a short pad of silica gel (80% EtOAc/hexane), the filtrate was concentrated in vacuo and the residue was crystallized from THF/hexane to provide 8f (251 mg, 81%) as a white solid. mp 174° C. (dec); IR (KBr) 3272 (br), 1779, 1727, 1464, 1224 $cm^{-1}$; $^1H$ NMR (DMSO-$d_6$) δ3.72 (1H, d, J=18.1 Hz), 3.75 (2H, s, $CH_2$), 3.98 (1H, d, J=18.1 Hz), 5.21 (1H, d, J=4.4 Hz), 5.73–5.79 (1H, m), 6.42 (2H, d, J=8.0 Hz), 6.93 (1H, s), 7.07 (1H, t, J=8.0 Hz), 7.25–7.44 (10H, m), 7.41 (1H, s), 9.22 (1H, d, J=8.0 Hz, NH), 12.17 (2H, s, OH); FDMS m/z 633 ($M^+$, $^{35}Cl$), 635

(M+, 37Cl); HRMS m/z Calcd for $C_{31}H_{25}{}^{35}ClN_3O_6S_2$ (M++1): 634.0873. Found: 634.0851.

EXAMPLE 20

[6R-[6A,7B(R*)]]-7-[[[2-(2,6-Dihydroxyphenyl)-4-thiazolyl]acetyl]amino]-8-oxo-5-thia-1-azabicyclo[4.2.0]oct-2-ene-2-carboxylic Acid Diphenylmethyl Ester (8g)

The procedure used for the preparation of 8a was repeated with 7c (200 mg, 0.546 mmol) and 5b (144 mg, 0.574 mmol), and Morpho CDI (301 mg, 0.710 mmol). After filtration through a short pad of silica gel (80% EtOAc/hexane), the filtrate was concentrated in vacuo and subject to chromatographic purification on silica gel (gradient EtOAc/hexane: 60–80%) to give 8g (180 mg, 55%) as a white solid, which was recrystallized from THF/hexane. mp 164.0°–166.0° C.; IR (KBr) 3292 (br), 1780, 1733, 1664, 1465 cm$^{-1}$; $^1$H NMR (DMSO-$d_6$) δ3.50–3.69 (2H, m), 3.77 (2H, s, $CH_2$), 5.06 (1H, d, J=4.8 Hz), 5.75–5.81 (1H, m), 6.42 (2H, d, J=8.1 Hz), 6.70–6.74 (1H, m), 6.87 (1H, s), 7.07 (1H, t, J=8.1 Hz), 7.18–7.53 (10H, m), 7.42 (1H, s), 9.16 (1H, d, J=8.2 Hz, NH), 12.18 (2H, s, OH); FDMS m/z 599 (M+); Anal. Calcd for $C_{31}H_{25}N_3O_6S_2$: C, 62.09; H, 4.20; N, 7.01. Found: C, 62.11; H, 4.16; N, 6.89.

EXAMPLE 21

[6R-[6A,7B(R*)]]-7-[[[2-(2,6-Dihydroxyphenyl)-4-thiazolyl]acetyl]amino]-3-methyl-8-oxo-5-thia-1-azabicyclo[4.2.0]oct-2-ene-2-carboxylic Acid Diphenylmethyl Ester (8h)

The procedure used for the preparation of 8a was repeated with 7d (200 mg, 0.526 mmol) and 5b (139 mg, 0.553 mmol), and Morpho CDI (310 mg, 0.732 mmol). After filtration through a short pad of silica gel (80% EtOAc/hexane), the filtrate was concentrated in vacuo and subject to chromatographic purification on silica gel (gradient EtOAc/$CH_2Cl_2$: 20–30%) to give 8h (203 mg, 63%) as a white solid, which was recrystallized from THF/hexane. mp 189° C. (dec); IR (KBr) 3273 (br), 1766, 1718, 1658, 1465, 1226 cm$^{-1}$; $^1$H NMR (DMSO-$d_6$) δ1.96 (3H, s, $CH_3$), 3.38 (1H, d, J=18.2 Hz), 3.55 (1H, d, J=18.2 Hz), 3.77 (2H, s, $CH_2$), 5.07 (1H, d, J=4.6 Hz), 5.66 (1H, dd, J=8.1 and 4.6 Hz), 6.42 (2H, d, J=8.1 Hz), 6.84 (1H, s), 7.07 (1H, t, J=8.1 Hz), 7.21–7.55 (11H, m), 9.13 (1H, d, J=8.1 Hz, NH), 12.18 (2H, s, OH); FDMS m/z 613 (M+), 614 (M++1); Anal. Calcd for $C_{32}H_{27}N_3O_6S_2$: C, 62.63; H, 4.43; N, 6.85. Found: C, 62.71; H, 4.50; N, 6.67.

EXAMPLE 22

[6R-[6A,7B(R*)]]-3-[(Acetyloxy)methyl]-7-[[[2-(3-hydroxy-2-pyridinyl)-4-thiazolyl]acetyl]amino]-8-oxo-5-thia-1-azabicyclo[4.2.0]oct-2-ene-2-carboxylic Acid Diphenylmethyl Ester (8i)

The procedure used for the preparation of 8a was repeated with 7a (219 mg, 0.500 mmol) and 5c (124 mg, 0.525 mmol), and Morpho CDI (275 mg, 0.650 mmol). After filtration through a short pad of silica gel (80% EtOAc/hexane), the filtrate was concentrated in vacuo and crystallized from THF/$CH_2Cl_2$/hexane to give 8i (236 mg, 72%) as a white solid. mp 176.5°–178.5° C.; IR (KBr) 3413 (br), 3292 (br), 1780, 1743, 1225 cm$^{-1}$; $^1$H NMR (DMSO-$d_6$) δ1.91 (3H, s, $CH_3$), 3.48 (1H, d, J=18.3 Hz), 3.62 (1H, d, J=18.3 Hz), 3.79 (2H, s, $CH_2$), 4.58 (1H, d, J=13.0 Hz), 4.81 (1H, d, J=13.0 Hz), 5.12 (1H, d, J=4.8 Hz), 5.77 (1H, dd, J=8.0 and 4.8 Hz), 6.88 (1H, s), 7.20–7.45 (12H, m), 7.59 (1H, s), 8.14 (1H, d, J=4.2 Hz), 9.19 (1H, d, J=8.0 Hz, NH), 11.63 (1H, s, OH); FDMS m/z 656 (M+), 657 (M++1); Anal. Calcd for $C_{33}H_{28}N_4O_7S_2$: C, 60.35; H, 4.30; N, 8.53. Found: C, 60.42; H, 4.44; N, 8.28.

EXAMPLE 23

[6R-[6A,7B(R*)]]-3-Chloro-7-[[[2-(3-hydroxy-2-pyridinyl)-4-thiazolyl]acetyl]amino]-8-oxo-5-thia-1-azabicyclo[4.2.0]oct-2-ene-2-carboxylic Acid Diphenylmethyl Ester (8j)

The procedure used for the preparation of 8a was repeated with 7b (200 mg, 0.499 mmol) and 5c (124 mg, 0.525 mmol), and Morpho CDI (275 mg, 0.650 mmol). After filtration through a short pad of silica gel (70% EtOAc/$CH_2Cl_2$), the filtrate was concentrated in vacuo and crystallized from EtOAc/hexane to give 8j (204 mg, 66%) as a brownish solid. mp 170° C. (dec); IR (KBr) 3284, 1781, 1728, 1660, 1223 cm$^{-1}$; $^1$H NMR (DMSO-$d_6$) δ3.72 (1H, d, J=18.1 Hz), 3.79 (2H, s, $CH_2$), 3.98 (1H, d, J=18.1 Hz), 5.21 (1H, d, J=4.8 Hz), 5.76 (1H, dd, J=8.1 and 4.8 Hz), 6.93 (1H, s), 7.20–7.48 (12H, m), 7.58 (1H, s), 8.14 (1H, d, J=4.2 Hz), 9.26 (1H, d, J=8.1 Hz, NH), 11.63 (1H, s, OH); FDMS m/z 619 (M++1, 35Cl), 621 (M++1, 37Cl); HRMS m/z Calcd for $C_{30}H_{24}{}^{35}ClN_4O_5S_2$ (M++1): 619.0877. Found: 619.0855.

EXAMPLE 24

[6R-[6A,7B(R*)]]-7-[[[2-(3-Hydroxy-2-pyridinyl)-4-thiazolyl]acetyl]amino]-8-oxo-5-thia-1-azabicyclo[4.2.0]oct-2-ene-2-carboxylic Acid Diphenylmethyl Ester (8k)

The procedure used for the preparation of 8a was repeated with 7c (200 mg, 0.546 mmol) and 5c (135 mg, 0.574 mmol), and Morpho CDI (301 mg, 0.710 mmol). After filtration through a short pad of silica gel (80% EtOAc/$CH_2Cl_2$), the filtrate was concentrated in vacuo and crystallized from THF/$CH_2Cl_2$/hexane to give 8k (197 mg, 62%) as a white solid. mp 195° C. (dec); IR (KBr) 3290, 1777, 1719, 1656 cm$^{-1}$; $^1$H NMR (DMSO-$d_6$) δ3.55–3.75 (2H, m), 3.83 (2H, s, $CH_2$), 5.08 (1H, d, J=5.0 Hz), 5.81 (1H, dd, J=8.1 and 5.0 Hz), 6.73–6.78 (1H, m), 6.90 (1H, s), 7.21–7.55 (12H, m), 7.62 (1H, s), 8.17 (1H, d, J=4.0 Hz), 9.24 (1H, d, J=8.1 Hz, NH), 11.67 (1H, s, OH); FDMS m/z 584 (M+), 585 (M++1); Anal. Calcd for $C_{30}H_{24}N_4O_5S_2$: C, 61.63; H, 4.14; N, 9.58. Found: C, 61.40; H, 4.34; N, 9.58.

EXAMPLE 25

[6R-[6A,7B(R*)]]-7-[[[2-(3-Hydroxy-2-pyridinyl)-4-thiazolyl]acetyl]amino]-3-methyl-8-oxo-5-thia-1-azabicyclo[4.2.0]oct-2-ene-2-carboxylic Acid Diphenylmethyl Ester (8l)

The procedure used for the preparation of 8a was repeated with 7d (200 mg, 0.526 mmol) and 5c (130 mg, 0.553 mmol), and Morpho CDI (290 mg, 0.684 mmol). After filtration through a short pad of silica gel (80% EtOAc/$CH_2Cl_2$), the filtrate was concentrated in vacuo and crystallized from THF/$CH_2Cl_2$/hexane to give 8l (205 mg, 65%) as a white solid. mp 174° C. (dec); IR (KBr) 3282, 1774, 1718, 1660, 1227 cm$^{-1}$; $^1$H NMR (DMSO-d$_6$) δ1.99 (3H, s, CH$_3$), 3.41 (1H, d, J=18.2 Hz), 3.58 (1H, d, J=18.2 Hz), 3.83 (2H, s, CH$_2$), 5.10 (1H, d, J=4.7 Hz), 5.69 (1H, dd, J=8.1 and 4.7 Hz), 6.87 (1H, s), 7.22 –7.52 (12H, m), 7.62 (1H, s), 8.17 (1H, d, J=4.3 Hz), 9.21 (1H, d, J=8.1 Hz, NH), 11.68 (1H, s, OH); FDMS m/z 598 (M$_+$), 599 (M$^+$+1); Anal. Calcd for C$_{31}$H$_{26}$N$_4$O$_5$S$_2$·(n-C$_6$H$_{14}$)$_{0.15}$: C, 62.64; H, 4.63; N, 9.16. Found: C, 62.42; H, 4.44; N, 8.92.

EXAMPLE 26

[6R-[6A,7B(R*)]]-3-[(Acetyloxy)methyl]-7-[[[2-(3-hydroxyphenyl)-4-thiazolyl]acetyl]amino]-8-oxo-5-thia-1-azabicyclo[4.2.0]oct-2-ene-2-Carboxylic Acid Diphenylmethyl Ester (8m)

The procedure used for the preparation of 8a was repeated with 7a (219 mg, 0.500 mmol) and 5d (118 mg, 0.502 mmol), and Morpho CDI (233 mg, 0.550 mmol). After filtration through a short pad of silica gel (80% EtOAc/hexane), the filtrate was concentrated in vacuo and subject to chromatographic purification on silica gel (gradient EtOAc/hexane: 60–80%) to give 8m (200 mg, 61%) as a white solid, which was recrystallized from EtOAc/hexane. mp 139.5°–141.0° C.; IR (KBr) 3420, 3281, 1782, 1713, 1225 cm$^{-1}$; $^1$H NMR (DMSO-d$_6$) δ1.91 (3H, s, CH$_3$), 3.50 (1H, d, J=18.3 Hz), 3.62 (1H, d, J=18.3 Hz), 3.73 (2H, s, CH$_2$), 4.59 (1H, d, J=13.0 Hz), 4.82 (1H, d, J=13.0 Hz), 5.13 (1H, d, J=4.9 Hz), 5.78 (1H, dd, J=8.3 and 4.9 Hz), 6.79–6.84 (1H, m), 6.88 (1H, s), 7.19–7.46 (14H, m), 9.10 (1H, d, J=8.3 Hz, NH), 9.67 (1H, s, OH); FABMS m/z 656 (M$^+$+1); Anal. Calcd for C$_{34}$H$_{29}$N$_3$O$_7$S$_2$: C, 62.28; H, 4.46; N, 6.41. Found: C, 62.33; H, 4.51; N, 6.23.

EXAMPLE 27

[6R-[6A,7B(R*)]]-7-[[[2-(3-Hydroxyphenyl)-4-thiazolyl]acetyl]amino]-8-oxo-5-thia-1-azabicyclo[4.2.0]oct-2-ene-2-carboxylic Acid Diphenylmethyl Ester (8n)

The procedure used for the preparation of 8a was repeated with 7c (252 mg, 0.689 mmol) and 5d (170 mg, 0.723 mmol), and Morpho CDI (350 mg, 0.827 mmol). After filtration through a short pad of silica gel (80% EtOAc/hexane), the filtrate was concentrated in vacuo and subject to chromatographic purification on silica gel (gradient EtOAc/hexane: 60–80%) to give 8n (253 mg, 63%) as a white solid, which was recrystallized from EtOAc/hexane. mp 152.0°–153.5° C.; IR (KBr) 3291 (br), 1754, 1735, 1661, 1276 cm$^{-1}$; $^1$H NMR (DMSO-d$_6$) δ3.57 (1H, dd, J=19.2 and 6.0 Hz), 3.66 (1H, dd, J=19.2 and 2.7 Hz), 3.74 (2H, s, CH$_2$), 5.07 (1H, d, J=5.0 Hz), 5.81 (1H, dd, J=8.3 and 5.0 Hz), 6.73 (1H, dd, J=6.0 and 2.7 Hz), 6.81 (1H, br d, J=7.8 Hz), 6.87 (1H, s), 7.19–7.53 (13H, m), 7.30 (1H, s), 9.11 (1H, d, J=8.3 Hz, NH), 9.68 (1H, s, OH); FDMS m/z 583 (M$^+$); Anal. Calcd for C$_{31}$H$_{25}$N$_3$O$_5$S$_2$: C, 63.79; H, 4.32; N, 7.20. Found: C, 63.85; H, 4.43; N, 6.96.

EXAMPLE 28

[6R-[6A,7B(R*)]]-3-[(Acetyloxy)methyl]-7-[[[2-(2-methoxyphenyl)-4-thiazolyl]acetyl]amino]-8-oxo-5-thia-1-azabicyclo[4.2.0]oct-2-ene-2-carboxylic Acid Diphenylmethyl Ester (8o)

The procedure used for the preparation of 8a was repeated with 7a (219 mg, 0.500 mmol) and 5e (131 mg, 0.525 mmol), and Morpho CDI (297 mg, 0.700 mmol). After filtration through a short pad of silica gel (80% EtOAc/hexane), the filtrate was concentrated in vacuo and subject to chromatographic purification on silica gel (gradient EtOAc/hexane: 60–80%) to give 8o (201 mg, 60%) as a colorless gum. IR (neat) 1780, 1723, 1223 cm$^{-1}$; $^1$H NMR (DMSO-d$_6$) δ1.91 (3H, s, CH$_3$), 3.50 (1H, d, J=18.3 Hz), 3.63 (1H, d, J=18.3 Hz), 3.74 (2H, s, CH$_2$), 3.96 (3H, s, CH$_3$), 4.59 (1H, d, J=13.0 Hz), 4.82 (1H, d, J=13.0 Hz), 5.13 (1H, d, J=5.0 Hz), 5.80 (1H, dd, J=8.3 and 5.0 Hz), 6.88 (1H, s), 7.04 (1H, t, J=7.4 Hz), 7.17–7.45 (13H, m), 8.22 (1H, dd, J=7.8 and 1.5 Hz), 9.11 (1H, d, J=8.3 Hz, NH); HRMS m/z Calcd for C$_{35}$H$_{32}$N$_3$O$_7$S$_2$ (M$^+$+1): 670.1682. Found: 670.1724.

EXAMPLE 29

[6R-[6A,7B(R*)]]-3-[(Acetyloxy)methyl]-7-[[[2-(2-hydroxyphenyl)-4-thiazolyl]acetyl]amino]-8-oxo-5-thia-1-azabicyclo[4.2.0]oct-2-ene-2-carboxylic Acid (9a)

To a stirred suspension of 8a (453 mg, 0.692 mmol) in dry ClCH$_2$CH$_2$Cl (12 mL) at 0° C. under nitrogen was added Et$_3$SiH (1.11 mL, 6.92 mmol) and trifluoroacetic acid (2.13 mL, 27.7 mmol). The resultant clear solution was stirred at 0° C. for 1.5 hr. After evaporation at ambient temperature in vacuo, the gummy residue was crystallized from THF/Et$_2$O/hexane to provide 9a (322 mg, 95%) as a white solid. mp 140° C. (dec); IR (KBr) 3528, 3470, 3290, 3300–2500 (br), 1765, 1743, 1724, 1662, 1224 cm$^{-1}$; $^1$H NMR (DMSO-d$_6$) δ2.01 (3H, s, CH$_3$), 3.47 (1H, d, J=18.1 Hz), 3.61 (1H, d, J=18.1 Hz), 3.77 (2H, s, CH$_2$), 4.67 (1H, d, J=12.8 Hz), 4.98 (1H, d, J=12.8 Hz), 5.09 (1H, d, J=4.8 Hz), 5.72 (1H, dd, J=8.1 and 4.8 Hz), 6.91 (1H, t, J=7.8 Hz), 6.99 (1H, d, J=7.8 Hz), 7.28 (1H, t, J=7.8 Hz), 7.43 (1H, s), 7.97 (1H, d, J=7.8 Hz), 9.12 (1H, d, J=8.1 Hz, NH), 11.32 (1H, s, OH), 13.65 (1H, br s, CO$_2$H); FDMS m/z 489 (M$^+$); Anal. Calcd for C$_{21}$H$_{19}$N$_3$O$_7$S$_2$: C, 51.53; H, 3.91; N, 8.58. Found: C, 51.80; H, 3.99; N, 8.33.

EXAMPLE 30

[6R-[6A,7B(R*)]]-3-Chloro-7-[[[2-(2-hydroxyphenyl)-4-thiazolyl]acetyl]amino]-8-oxo-5-thia-1-azabicyclo[4.2.0]oct-2-ene-2-carboxylic Acid (9b)

The procedure used for the preparation of 9a was repeated with 8b (390 mg, crude from previous reaction), Et$_3$SiH (0.80 mL, 5.0 mmol), and trifluoroacetic acid (1.50 mL, 19.5 mmol) in dry ClCH$_2$CH$_2$Cl (8 mL) at 0° C. under nitrogen to give 9b (50.0 mg, 35% for two steps) as a white solid after chromatographic separation on RP C-18 (gradient CH$_3$CN/H$_2$O: 25–30%, containing 1% HOAc). mp 155° C. (dec); IR (KBr) 3600–2800 (br), 3280, 1780, 1661 cm$^{-1}$; $^1$H NMR (DMSO-d$_6$) δ3.63 (1H, d, J=18.0 Hz), 3.74 (2H, s, CH$_2$), 3.93 (1H, d, J=18.0 Hz), 5.15(1H, d, J=4.7 Hz), 5.70 (1H, dd, J=8.0 and 4.7 Hz), 6.88 (1H, t, J=7.7 Hz), 6.96 (1H, d, J=7.7 Hz), 7.25 (1H, t, J=7.7 Hz), 7.40 (1H, s), 7.94 (1H, d, J=7.7 Hz), 9.16 (1H, d, J=8.0 Hz, NH), 11.30 (1H, s, OH), 13.80 (1H, br s, CO$_2$H); FDMS m/z 451 (M$^+$, $^{35}$Cl), 452 (M$^+$+1, $^{35}$Cl), 453 (M$^+$, $^{37}$Cl), 454 (M$^+$+1, $^{37}$Cl); Anal., Calcd for C$_{18}$H$_{14}$ClN$_3$O$_5$S$_2$: C, 47.84; H, 3.12; N, 9.30. Found: C, 48.12; H, 3.16; N, 9.36.

EXAMPLE 31

[6R-[6A,7B(R*)]]-7-[[[2-(2-Hydroxyphenyl)-4-thiazolyl]acetyl]amino]-8-oxo-5-thia-1-azabicyclo[4.2.0]oct-2-ene-2-carboxylic Acid (9c)

The procedure used for the preparation of 9a was repeated with 8c (184 mg, 0.316 mmol), $Et_3SiH$ (0.505 mL, 3.16 mmol), and trifluoroacetic acid (0.972 mL, 12.6 mmol) in dry $ClCH_2CH_2Cl$ (4 mL) at 0° C. under nitrogen to give 9c (132 mg, 100%) as a white solid after crystallization from $THF/Et_2O$/hexane. mp 185° C. (dec); IR (KBr) 3700–2800 (br), 3291, 1768, 1710, 1659, 1230 $cm^{-1}$; $^1H$ NMR (DMSO-$d_6$) δ3.48 (1H, dd, J=19.0 and 6.0 Hz), 3.59 (1H, dd, J=19.0 and 2.6 Hz), 3.75 (2H, s, $CH_2$), 5.01(1H, d, J=4.9 Hz), 5.72 (1H, dd, J=8.2 and 4.9 Hz), 6.45 (1H, dd, J=6.0 and 2.6 Hz), 6.88 (1H, t, J=7.8 Hz), 6.96 (1H, d, J=7.8 Hz), 7.25 (1H, t, J=7.8 Hz), 7.41 (1H, s), 7.94 (1H, d, J=7.8 Hz), 9.08 (1H, d, J=8.2 Hz, NH), 11.30 (1H, s, OH), 13.14 (1H, br s, $CO_2H$); FDMS m/z 417 ($M_+$), 418 ($M^++1$); Anal. Calcd for $C_{18}H_{15}N_3O_5S_2 \cdot (C_4H_8O)_{0.20}$: C, 52.28; H, 3.87; N, 9.73. Found: C, 52.41; H, 3.62; N, 9.71.

EXAMPLE 32

[6R-[6A,7B(R*)]]-7-[[[2-(2-Hydroxyphenyl)-4-thiazolyl]acetyl]amino]-3-methyl-8-oxo-5-thia-1-azabicyclo[4.2.0]oct-2-ene-2-carboxylic Acid (9d)

The procedure used for the preparation of 9a was repeated with 8d (50 mg, crude from previous reaction), $Et_3SiH$ (0.134 mL, 0.84 mmol), and trifluoroacetic acid (0.260 mL, 3.36 mmol) in dry $ClCH_2CH_2Cl$ (2 mL) at 0° C. under nitrogen to give 9d (31 mg, 14% for two steps) as a white solid after chromatographic separation on RP C-18 (gradient $CH_3CN/H_2O$: 20–40%, containing 1% HOAc). mp 150° C. (dec); IR (KBr) 3600–2600 (br), 3277, 1772, 1659, 1224 $cm^{-1}$; $^1H$ NMR (DMSO-$d_6$) δ2.00 (3H, s, $CH_3$), 3.33 (1H, d, J=18.1), 3.54 (1H, d, J=18.1 Hz), 3.77 (2H, s, $CH_2$), 5.03 (1H, d, J=4.6 Hz), 5.61 (1H, dd, J=8.1 and 4.6 Hz), 6.91 (1H, t, J=7.8 Hz), 6.99 (1H, d, J=7.8 Hz), 7.28 (1H, t, J=7.8 Hz), 7.43 (1H, s), 7.97 (1H, d, J=7.8 Hz), 9.07 (1H, d, J=8.1 Hz, NH), 11.35 (1H, br s, OH), 13.25 (1H, br s, $CO_2H$); FDMS m/z 431 ($M_+$); Anal. Calcd for $C_{19}H_{17}N_3O_5S_2$: C, 52.89; H, 3.97; N, 9.74. Found: C, 52.94; H, 3.81; N, 9.51.

EXAMPLE 33

[6R-[6A,7B(R*)]]-3-[(Acetyloxy)methyl]-7-[[[2-(2,6-dihydroxyphenyl)-4-thiazolyl]acetyl]amino]-8-oxo-5-thia-1-azabicyclo[4.2.0]oct-2-ene-2-carboxylic Acid (9e)

The procedure used for the preparation of 9a was repeated with 8e (181 mg, 0.270 mmol), $Et_3SiH$ (0.431 mL, 2.70 mmol), and trifluoroacetic acid (0.832 mL, 10.8 mmol) in dry $ClCH_2CH_2Cl$ (6 mL) at 0° C. under nitrogen to give 9e (120 mg, 88%) as a white solid after crystallization from $EtOAc/CH_2Cl_2$/hexane. mp 145° C. (dec); IR (KBr) 3650–2500 (br), 1775, 1736, 1466, 1237 $cm^{-1}$; $^1H$ NMR (DMSO-$d_6$) δ1.98 (3H, s, $CH_3$), 3.43 (1H, d, J=18.1 Hz), 3.58 (1H, d, J=18.1 Hz), 3.76 (2H, s, $CH_2$), 4.64 (1H, d, J=12.8 Hz), 4.95 (1H, d, J=12.8 Hz), 5.05 (1H, d, J=5.0 Hz), 5.64–5.70 (1H, m), 6.42 (2H, d, J=8.0 Hz), 7.07 (1H, t, J=8.0 Hz), 7.41 (1H, s), 9.12 (1H, d, J=8.1 Hz, NH), 12.17 (2H, br s, OH), 13.60 (1H, br s, $CO_2H$); FDMS m/z 505 ($M_+$), 506 ($M^++1$); Anal. Calcd for $C_{21}H_{19}N_3O_8S_2$: C, 49.89; H, 3.79; N, 8.31. Found: C, 50.15; H, 3.79; N, 8.60.

EXAMPLE 34

[6R-[6A, 7B(R*)]]-3-Chloro-7-[[[2-(2,6-dihydroxyphenyl)-4-thiazolyl]acetyl]amino]-8-oxo-5-thia-1-azabicyclo[4.2.0]oct-2-ene-2-carboxylic Acid (9f)

The procedure used for the preparation of 9a was repeated with 8f (196 mg, 0.309 mmol), $Et_3SiH$ (0.494 mL, 3.09 mmol), and trifluoroacetic acid (0.952 mL, 12.4 mmol) in dry $ClCH_2CH_2Cl$ (7 mL) at 0° C. under nitrogen to give 9f (137 mg, 95%) as a white solid after crystallization from $THF/CH_2Cl_2$/hexane. mp 157° C. (dec); IR (KBr) 3600–2500 (br), 1781, 1670 $cm^{-1}$; $^1H$ NMR (DMSO-$d_6$) δ3.64 (1H, d, J=18.0 Hz), 3.75 (2H, s, $CH_2$), 3.93 (1H, d, J=18.0 Hz), 5.15 (1H, d, J=4.7 Hz), 5.65–5.71 (1H, m), 6.42 (2H, d, J=8.1 Hz), 7.07 (1H, t, J=8.1 Hz), 7.41 (1H, s), 9.19 (1H, d, J=8.0 Hz, NH), 12.20 (2H, br s, OH), 13.80 (1H, br s, $CO_2H$); FDMS m/z 467 ($M^+$, $^{35}Cl$), 468 ($M^++1$, $^{35}Cl$), 469 ($M^+$, $^{37}Cl$), 470 ($M^++1$, $^{37}Cl$); Anal. Calcd for $C_{18}H_{14}ClN_3O_6S_2$: C, 46.21; H, 3.02; N, 8.98. Found: C, 46.36; H, 3.20; N, 8.68.

EXAMPLE 35

[6R-[6A,7B(R*)]]-7-[[[2-(2,6-Dihydroxyphenyl)-4-thiazolyl]acetyl]amino]-8-oxo-5-thia-1-azabicyclo[4.2.0]oct-2-ene-2-carboxylic Acid (9g)

The procedure used for the preparation of 9a was repeated with 8g (145 mg, 0.242 mmol), $Et_3SiH$ (0.387 mL, 2.42 mmol), and trifluoroacetic acid (0.746 mL, 9.68 mmol) in dry $ClCH_2CH_2Cl$ (6 mL) at 0° C. under nitrogen to give 9g (90.5 mg, 86%) as a white solid after crystallization from $THF/CH_2Cl_2$/hexane. mp 165° C. (dec); IR (KBr) 3550–2550 (br), 3282, 1779, 1725, 1665, 1469, 1235 $cm^{-1}$; $^1H$ NMR (DMSO-$d_6$) δ3.43–3.62 (2H, m), 3.76 (2H, s, $CH_2$), 5.00 (1H, d, J=4.8 Hz), 5.67–5.73 (1H, m), 6.42 (3H, d, J=8.1 Hz), 7.07 (1H, t, J=8.1 Hz), 7.41 (1H, s), 9.11 (1H, d, J=8.2 Hz, NH), 12.17 (2H, br s, OH), 13.16 (1H, br s, $CO_2H$); FDMS m/z 433 ($M_+$), 434 ($M^++1$); HRMS m/z Calcd for $C_{18}H_{16}N_3O_6S_2$ ($M^++1$): 434.0481, Found: 434.0448.

EXAMPLE 36

[6R-[6A, 7B(R*)]]-7-[[[2-(2,6-Dihydroxyphenyl)-4-thiazolyl]acetyl]amino]-3-methyl-8-oxo-5-thia-1-azabicyclo[4.2.0]oct-2-ene-2-carboxylic Acid (9h)

The procedure used for the preparation of 9a was repeated with 8h (169 mg, 0.276 mmol), $Et_3SiH$ (0.441 mL, 2.76 mmol), and trifluoroacetic acid (0.849 mL, 11.0 mmol) in dry $ClCH_2CH_2Cl$ (6 mL) at 0° C. under nitrogen to give 9h (121 mg, 98%) as a white solid after crystallization from THF/hexane. mp 155° C. (dec); IR (KBr) 3500–2500 (br), 1768, 1670, 1467 $cm^{-1}$; $^1H$ NMR (DMSO-$d_6$) δ1.97 (3H, s, $CH_3$), 3.31 (1H, d, J=18.0 Hz), 3.51 (1H, d, J=18.0 Hz), 3.76 (2H, s, $CH_2$), 5.00 (1H, d, J=4.5 Hz), 5.57 (1H, dd, J=8.0 and 4.5 Hz), 6.42 (2H, d, J=8.1 Hz), 7.07 (1H, t, J=8.1 Hz), 7.41 (1H, s), 9.07 (1H, d, J=8.0 Hz, NH), 12.20 (2H, br s, OH), 13.20 (1H, br s, $CO_2H$); FDMS m/z 448 ($M^++1$); HRMS m/z Calcd for $C_{19}H_{18}N_3O_6S_2$ ($M^++1$): 448.0637, Found: 448.0607.

EXAMPLE 37

**[6R-[6A,7B(R*)]]-3-[(Acetyloxy)methyl]-7-[[[2-(3-hydroxy-2-pyridinyl)-4-thiazolyl]acetyl]amino]-8-oxo-5-thia-1-azabicyclo[4.2.0]oct-2-ene-2-carboxylic Acid (9i)**

The procedure used for the preparation of 9a was repeated with 8i (170 mg, 0.259 mmol), $Et_3SiH$ (0.414 mL, 2.59 mmol), and trifluoroacetic acid (0.798 mL, 10.4 mmol) in dry $ClCH_2CH_2Cl$ (6 mL) at 0° C. under nitrogen to give 9i (121 mg, 95%) as a white solid after crystallization from $THF/CH_2Cl_2$/hexane. mp 165° C. (dec); IR (KBr) 3600–2800 (br), 3420, 3278, 1784, 1739, 1668, 1231 $cm^{-1}$; $^1H$ NMR (DMSO-$d_6$) δ1.98 (3H, s, $CH_3$), 3.42 (1H, d, J=18.0 Hz), 3.57 (1H, d, J=18.0 Hz), 3.79 (2H, s, $CH_2$), 4.64 (1H, d, J=12.8 Hz), 4.95 (1H, d, J=12.8 Hz), 5.05 (1H, d, J=4.3 Hz), 5.64–5.70 (1H, m), 7.33–7.39 (1H, m), 7.44 (1H, d, J=8.4 Hz), 7.58 (1H, s), 8.14 (1H, d, J=4.0 Hz), 9.16 (1H, d, J=8.1 Hz, NH), 11.63 (1H, s, OH), 13.61 (1H, br s, $CO_2H$); FDMS m/z 491 (M$^+$+1); Anal. Calcd for $C_{20}H_{18}N_4O_7S_2 \cdot (C_6H_{14})_{0.08}$: C, 49.45; H, 3.87; N, 11.26. Found: C, 49.39; H, 3.82; N, 11.16.

EXAMPLE 38

**[6R-[6A, 7B(R*)]]-3-Chloro-7-[[[2-(3-hydroxy-2-pyridinyl)-4-thiazolyl]acetyl]amino]-8-oxo-5-thia-1-azabicyclo[4.2.0]oct-2-ene-2-carboxylic Acid (9j)**

The procedure used for the preparation of 9a was repeated with 8j (186 mg, 0.301 mmol), $Et_3SiH$ (0.480 mL, 3.01 mmol), and trifluoroacetic acid (0.927 mL, 12.0 mmol) in dry $ClCH_2CH_2Cl$ (6 mL) at 0° C. under nitrogen to give 9j (123 mg, 90%) as a brownish solid after crystallization from $THF/CH_2Cl_2$/hexane. mp 175° C. (dec); IR (KBr) 3600–2700 (br), 3277, 1780, 1730, 1663 $cm^{-1}$; $^1H$ NMR (DMSO-$d_6$) δ3.63 (1H, d, J=18.0 Hz), 3.78 (1H, s, $CH_2$), 3.98 (1H, d, J=18.0 Hz), 5.15 (1H, d, J=4.8 Hz), 5.69 (1H, dd, J=8.1 and 4.8 Hz), 7.37 (1H, dd, J=8.4 and 4.3 Hz), 7.44 (1H, dd, J=8.4 and 1.1 Hz), 7.58 (1H, s), 8.14 (1H, dd, J=4.3 and 1.1 Hz), 9.23 (1H, d, J=8.1 Hz, NH), 11.62 (1H, s, OH), 13.80 (1H, br s, $CO_2H$); FDMS m/z 453 (M$^+$+1, $^{35}Cl$), 455 (M$^+$+1, $^{37}Cl$); HRMS m/z Calcd for $C_{17}H_{14}^{35}ClN_4O_5S_2$ (M$^+$+1): 453.0094, Found: 453.0090.

EXAMPLE 39

**[6R-[6A,7B(R*)]]-7-[[[2-(3-Hydroxy-2-pyridinyl)-4-thiazolyl]acetyl]amino]-8-oxo-5-thia-1-azabicyclo[4.2.0]oct-2-ene-2-carboxylic Acid (9k)**

The procedure used for the preparation of 9a was repeated with 8k (129 mg, 0.221 mmol), $Et_3SiH$ (0.353 mL, 2.21 mmol), and trifluoroacetic acid (0.681 mL, 8.84 mmol) in dry $ClCH_2CH_2Cl$ (6 mL) at 0° C. under nitrogen to give 9k (79.1 mg, 86%) as a yellowish solid after crystallization from $THF/CH_2Cl_2$/hexane. mp 170° C. (dec); IR (KBr) 3600–2800 (br), 3276, 1776, 1723, 1663 $cm^{-1}$; $^1H$ NMR (DMSO-$d_6$) δ3.48 (1H, dd, J=18.9 and 6.0 Hz), 3.58 (1H, dd, J=18.9 and 2.5 Hz), 3.79 (2H, s, $CH_2$), 5.00 (1H, d, J=5.0 Hz), 5.70 (1H, dd, J=8.1 and 5.0 Hz), 6.44 (1H, dd, J=6.0 and 2.5 Hz), 7.37 (1H, dd, J=8.1 and 4.2 Hz), 7.44 (1H, d, J=8.1 Hz), 7.58 (1H, s), 8.14 (1H, d, J=4.2 Hz), 9.15 (1H, d, J=8.1 Hz, NH), 11.64 (1H, s, OH), 13.20 (1H, br s, $CO_2H$); FDMS m/z 419 (M$^+$+1); Anal. Calcd for $C_{17}H_{14}N_4O_5S_2 \cdot (C_4H_8O)$ 0.17: C, 49.30; H, 3.59; N, 13.01. Found: C, 49.13; H, 3.38; N, 12.78.

EXAMPLE 40

**6R-[6A, 7B(R*)]]-7-[[[2-(3-Hydroxy-2-pyridinyl)-4-thiazolyl]acetyl]amino]-3-methyl-8-oxo-5-thia-1-azabicyclo[4.2.0]oct-2-ene-2-carboxylic Acid (9l)**

The procedure used for the preparation of 9a was repeated with 8l (167 mg, 0.279 mmol), $Et_3SiH$ (0.446 mL, 2.79 mmol), and trifluoroacetic acid (0.860 mL, 11.2 mmol) in dry $ClCH_2CH_2Cl$ (6 mL) at 0° C. under nitrogen to give 9l (112 mg, 93%) as a yellowish solid after crystallization from $THF/CH_2Cl_2$/hexane. mp 180° C. (dec); IR (KBr) 3540–2540 (br), 3280, 1774, 1725, 1661 $cm^{-1}$; $^1H$ NMR (DMSO-$d_6$) δ1.97 (3H, s, $CH_3$), 3.30 (1H, d, J=18.0 Hz), 3.51 (1H, d, J=18.0 Hz), 3.79 (2H, s, $CH_2$), 4.99 (1H, d, J=4.6 Hz), 5.56 (1H, dd, J=8.1 and 4.6 Hz), 7.37 (1H, dd, J=8.4 and 4.3 Hz), 7.44 (1H, dd, J=8.4 and 1.0 Hz), 7.58 (1H, s), 8.14 (1H, dd, J=4.3 and 1.0 Hz), 9.11 (1H, d, J=8.1 Hz, NH), 11.64 (1H, s, OH), 13.12 (1H, br s, $CO_2H$); FDMS m/z 432 (M$_+$), 433 (M$^+$+1); Anal. Calcd for $C_{18}H_{16}N_4O_5S_2$: C, 49.99; H, 3.73; N, 12.95. Found: C, 50.24; H, 3.58; N, 12.68.

EXAMPLE 41

**[6R-[6A,7B(R*)]]-3-[(Acetyloxy)methyl]-7-[[[2-(3-hydroxyphenyl)-4-thiazolyl]acetyl]amino]-8-oxo-5-thia-1-azabicyclo[4.2.0]oct-2-ene-2-carboxylic Acid (9m)**

The procedure used for the preparation of 9a was repeated with 8m (157 mg, 0.240 mmol), $Et_3SiH$ (0.383 mL, 2.40 mmol), and trifluoroacetic acid (0.739 mL, 9.59 mmol) in dry $ClCH_2CH_2Cl$ (6 mL) at 0° C. under nitrogen to give 9m (113 mg, 96%) as a white solid after crystallization from $THF/CH_2Cl_2$/hexane. mp 140° C. (dec); IR (KBr) 3600–2650 (br), 3286, 1782, 1738, 1671, 1230 $cm^{-1}$; $^1H$ NMR (DMSO-$d_6$) δ1.98 (3H, s, $CH_3$), 3.44 (1H, d, J=18.1 Hz), 3.59 (1H, d, J=18.1 Hz), 3.72 (2H, s, $CH_2$), 4.64 (1H, d, J=12.8 Hz), 4.96 (1H, d, J=12.8 Hz), 5.07 (1H, d, J=4.8 Hz), 5.69 (1H, dd, J=8.2 and 4.8 Hz), 6.82 (1H, d, J=7.8 Hz), 7.22 (1H, t, J=7.8 Hz), 7.28 (1H, d, J=7.8 Hz), 7.29 (1H, s), 7.39 (1H, s), 9.06 (1H, d, J=8.2 Hz, NH), 9.68 (1H, br s, OH), 13.62 (1H, br s, $CO_2H$); FDMS m/z 490 (M$^+$+1); Anal. Calcd for $C_{21}H_{19}N_3O_7S_2 \cdot (C_4H_8O)_{0.25}$: C, 52.06; H, 4.17; N, 8.28. Found: C, 51.95; H, 3.94; N, 8.04.

EXAMPLE 42

**[6R-[6A,7B(R*)]]-7-[[[2-(3-Hydroxyphenyl)-4-thiazolyl]acetyl]amino]-8-oxo-5-thia-1-azabicyclo[4.2.0]oct-2-ene-2-carboxylic Acid (9n)**

The procedure used for the preparation of 9a was repeated with 8n (152 mg, 0.261 mmol), $Et_3SiH$ (0.417 mL, 2.61 mmol), and trifluoroacetic acid (0.804 mL, 10.4 mmol) in dry $ClCH_2CH_2Cl$ (4 mL) at 0° C. under nitrogen to give 9n (108 mg, 99%) as a white solid after crystallization from $THF/Et_2O$/hexane. mp 195° C. (dec); IR (KBr) 3600–2600 (br), 3343, 1787, 1682, 1532 $cm^{-1}$; $^1H$ NMR (DMSO-$d_6$) δ3.49 (1H, dd, J=19.0 and 6.0 Hz), 3.59 (1H, dd, J=19.0 and 2.6 Hz), 3.73 (2H, s, $CH_2$), 5.01(1H, d, J=4.9 Hz), 5.73 (1H, dd, J=8.3 and 4.9 Hz), 6.45 (1H, dd, J=6.0 and 2.6 Hz), 6.88 (1H, d, J=7.8 Hz), 7.22 (1H, t, J=7.8 Hz), 7.28 (1H, d, J=7.8

Hz), 7.29 (1H, s), 7.38 (1H, s), 9.05 (1H, d, J=8.3 Hz, NH), 9.68 (1H, s, OH), 13.15 (1H, br s, CO$_2$H); FDMS m/z 417 (M$^+$), 418 (M$^+$+1); Anal. Calcd for C$_{18}$H$_{15}$N$_3$O$_5$S$_2$: C, 51.79; H, 3.62; N, 10.07. Found: C, 51.95; H, 3.66; N, 9.80.

EXAMPLE 43

[6R-[6A,7B(R*)]]-3-[(Acetyloxy)methyl]-7-[[[2-(2-methoxyphenyl)-4-thiazolyl]acetyl]amino]-8-oxo-5-thia-1-azabicyclo[4.2.0]oct-2-ene-2-carboxylic Acid (9o)

The procedure used for the preparation of 9a was repeated with 8o (193 mg, 0.288 mmol), Et$_3$SiH (0.461 mL, 2.88 mmol), and trifluoroacetic acid (0.887 mL, 11.5 mmol) in dry ClCH$_2$CH$_2$Cl (7 mL) at 0° C. under nitrogen to give 9o (106 mg, 73%) as a white solid after crystallization from THF/CH$_2$Cl$_2$/hexane. mp 178° C. (dec); IR (KBr) 3550–2800 (br), 3278, 1785, 1735, 1667, 1256 cm$^{-1}$; $^1$H NMR (DMSO-d$_6$) δ1.98 (3H, s, CH$_3$), 3.45 (1H, d, J=18.1 Hz), 3.59 (1H, d, J=18.1 Hz), 3.74 (2H, s, CH$_2$), 3.96 (3H, s, CH$_3$), 4.65 (1H, d, J=12.8 Hz), 4.96 (1H, d, J=12.8 Hz), 5.07 (1H, d, J=4.8 Hz), 5.71 (1H, dd, J=8.1 and 4.8 Hz), 7.04 (1H, t, J=7.5 Hz), 7.19 (1H, d, J=8.3 Hz), 7.37–7.42 (1H, m), 7.41 (1H, s), 8.22 (1H, d, J=7.5 Hz), 9.06 (1H, d, J=8.1 Hz, NH), 13.62 (1H, br s, CO$_2$H); FDMS m/z 504 (M$^+$+1); Anal. Calcd for C$_{22}$H$_{21}$N$_3$O$_7$S$_2$: C, 52.48; H, 4.20; N, 8.34. Found: C, 52.72; H, 4.27; N, 8.10.

I claim:
1. The compound of the formula

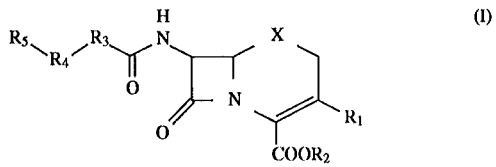

wherein X is O;

R$_1$ is hydrogen, hydroxy, halo, trifluoromethyl, C$_2$F$_5$, C$_1$–C$_6$ alkyl, C$_1$–C$_6$ substituted alkyl, C$_1$–C$_6$ alkenyl, C$_1$–C$_6$ alkynyl, CH$_2$O(CO)R', CH$_2$O(CO)NH$_2$, CO$_2$R', thio(C$_1$–C$_6$)alkyl, thio(C$_1$–C$_6$)alkenyl, oxo(C$_1$–C$_6$)alkyl, phosphine oxide, quaternary ammonium group, substituted or unsubstituted thiazolothio, or oxo(C$_1$–C$_6$)alkenyl; wherein R' is hydrogen, C$_1$–C$_6$ alkyl, or C$_1$–C$_6$ alkenyl;

R$_2$ is hydrogen or a carboxy protecting group;

R$_3$ is

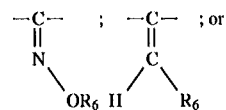

(CH$_2$)$_n$;

wherein R$_6$ is hydrogen Me, CH$_2$F, CF$_3$, C$_2$H$_5$, CH$_2$CH$_2$F, CH$_2$CF$_3$, C$_2$F$_5$, CH$_2$CO$_2$R', CH$_2$CONH$_2$, C(Me)$_2$CO$_2$R', or C(Me)$_2$CONH$_2$; and n is 0–5;

R$_4$ is

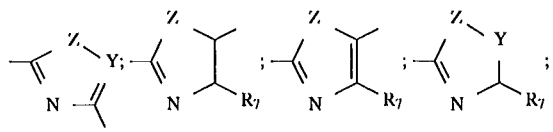

wherein Z is O, S, NH, or CH$_2$; Y is CH or N; and R$_7$ is hydrogen, C$_1$–C$_6$ alkyl, CONH$_2$, or CO$_2$R'; and R$_5$ is

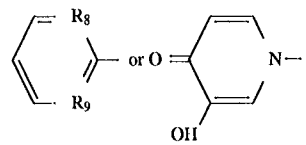

wherein R$_8$ is CH, N, COH, CO(C$_1$–C$_6$ alkyl), CSH, or CNH$_2$; and R$_9$ is R$_8$ as defined; said R$_5$ optionally substituted 1–4 times with halo, OH, SH, NH$_2$, NO$_2$, CH$_3$, C$_2$H$_5$, CO$_2$R', CONH$_2$, SO$_3$H, or SO$_2$NHR'; and salts thereof.

2. A pharmaceutical composition which comprises a compound of claim 1 combined with one or more pharmaceutically acceptable carriers or diluents.

3. A method for treating bacterial infections in man or other animal which comprises administering a compound of claim 1 to said man or animal.

* * * * *